US009238684B2

(12) United States Patent
Arya et al.

(10) Patent No.: US 9,238,684 B2
(45) Date of Patent: Jan. 19, 2016

(54) SPANX-B POLYPEPTIDES AND THEIR USE

(71) Applicant: The United States of America, as represented by the Secretary of the Department of Health and Human Services, Washington, DC (US)

(72) Inventors: Bira Arya, Ellicott City, MD (US); Vladimir L. Larionov, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/155,230

(22) Filed: Jan. 14, 2014

(65) Prior Publication Data
US 2014/0127246 A1 May 8, 2014

Related U.S. Application Data

(62) Division of application No. 13/203,042, filed as application No. PCT/US2010/025633 on Feb. 26, 2010, now Pat. No. 8,664,183.

(60) Provisional application No. 61/156,435, filed on Feb. 27, 2009.

(51) Int. Cl.
| *A61K 38/00* | (2006.01) |
|---|---|
| *A61K 38/04* | (2006.01) |
| *A61K 38/08* | (2006.01) |
| *A61K 38/10* | (2006.01) |
| *C07K 14/47* | (2006.01) |
| *A61K 39/00* | (2006.01) |
| *C07K 14/82* | (2006.01) |
| *A61K 45/06* | (2006.01) |

(52) U.S. Cl.
CPC ......... *C07K 14/4748* (2013.01); *A61K 39/0011* (2013.01); *A61K 45/06* (2013.01); *C07K 14/82* (2013.01); *A61K 2039/5158* (2013.01); *A61K 2039/53* (2013.01)

(58) Field of Classification Search
None
See application file for complete search history.

(56) References Cited

U.S. PATENT DOCUMENTS

| 6,639,063 B1 | 10/2003 | Edwards et al. |
| 2003/0180298 A1 | 9/2003 | Old et al. |
| 2004/0214248 A1* | 10/2004 | Roberts et al. ............... 435/7.23 |
| 2006/0115817 A1 | 6/2006 | Lim et al. |
| 2006/0257880 A1 | 11/2006 | Rees et al. |
| 2008/0213258 A1 | 9/2008 | Massague et al. |

FOREIGN PATENT DOCUMENTS

| WO | WO 00/24870 | 5/2000 |
| WO | WO 2004/020607 | 3/2004 |
| WO | WO 2006/065938 | 6/2006 |

OTHER PUBLICATIONS

Almanzar et al., "Sperm-Derived SPANX-B is a Clinically Relevant Tumor Antigen That is Expressed in Human Tumors and Readily Recognized by Human CD4+ and CD8+ T Cells," *Clinical Cancer Research*, vol. 15, No. 6, pp. 1954-1963, 2009.
Biragyn, "Immunotherapeutic Potency of Embryonic and Sperm-Expressed Antigens," presented at Advances in Cancer Vaccines Meeting, Aug. 13-15, 2008 (12 pages).
Cytotoxic T Cell, at http://en.wikipedia.org/wiki/Cytotoxic_T_cell; accessed Apr. 5, 2013.
Frank et al., "Cellular immune responses against the cancer-testis antigen SPAN-XB in healthy donors and patients with multiple myeloma," *Leukemia & Lymphoma*, vol. 49, No. 4, pp. 779-785, 2008.
Kouprina et al., "The SPANX gene gamily of cancer/testis-specific antigens: Rapid evolution and amplification in African great apes and hominids," *Proc. Natl. Acad. Sci. USA*, vol. 101, No. 9, pp. 3077-3082, 2004.
Parker et al., "Scheme for ranking potential HLA-A2 binding peptides based on independent binding of individual peptide side-chains," *J. Immunol.*, vol. 152, pp. 163-175, 1994.
Wang et al., "Gene expression and immunologic consequence of SPAN-Xb in myeloma and other hematologic malignancies," *Blood*, vol. 101, No. 3, pp. 955-960, 2003.
Westbrook et al., "Differential Nuclear Localization of the Cancer/Testis-Associated Protein, SPAN-X/CTp11, in Transfected Cells and in 50% of Human Spermatozoa," *Biology of Reproduction*, vol. 64, pp. 345-358, 2001.
Westbrook et al., "Genomic Organization, Incidence, and Localization of the SPAN-X Family of Cancer-Testis Antigens in Melanoma Tumors and Cell Lines," *Clinical Cancer Research*, vol. 10, pp. 101-112, 2004.
Zendman et al., "The human *SPANX* multigene family: genomic organization, alignment and expression in male germ cells and tumor cell lines," *Gene*, vol. 309, pp. 125-133, 2003.

\* cited by examiner

*Primary Examiner* — Elizabeth C Kemmerer
(74) *Attorney, Agent, or Firm* — Klarquist Sparkman, LLP

(57) ABSTRACT

It is disclosed herein that SPANX-B is uniquely expressed in a number of human tumors and that SPANX-B is an immunogenic antigen that is recognized by human T cells inducing helper CD4+ and cytolytic CD8+ T cell responses. Specific SPANX-B polypeptides and polynucleotides are disclosed that can be used to generate an immune response. In several embodiments, these polypeptides can be used for the treatment of a variety of cancers, including melanoma, colon carcinoma, ovarian cancer, breast cancer, myeloma, lung carcinoma and renal cancer.

11 Claims, 14 Drawing Sheets

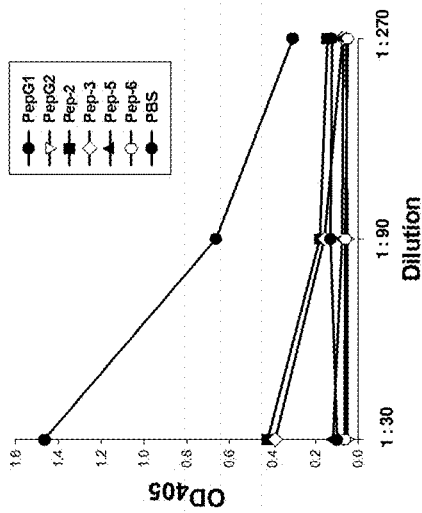

FIG. 1A

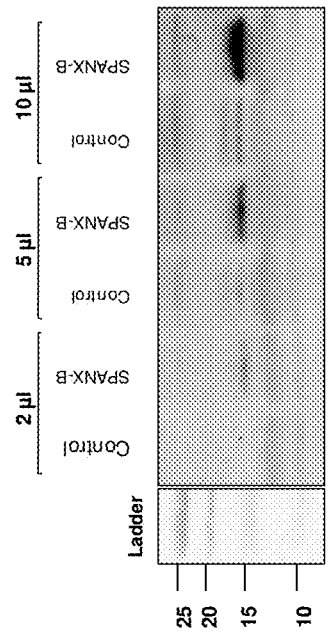

| SPANX-B | MGQQSSVRRLKRSVPCESNEANEANEANKTMPETPTGDSDPQPAPKKMKTSESSTILVVRYRRNVKRTSPEELVNDHARENRINPDQMEEEFIEITTERPKK (SEQ. ID. NO: 1) |
|---|---|
| Pep-1 | LQMEEEEFM (SEQ. ID. NO: 18) |
| Pep-2 | GQQSSVRRL (SEQ. ID. NO: 2) |
| Pep-3 | EANEANKTM (SEQ. ID. NO: 3) |
| Pep-4 | LVVRYRRNV (SEQ. ID. NO: 4) |
| Pep-5 | RSVPCESNE VNETMPETPTGDSDP (SEQ. ID. NO: 5) |
| Pep-6 | QPAPKKMKTSESSTILVVRYRRNV (SEQ. ID. NO: 6) |
| Pep-G1 | KRSVPCESNEANEANEANKTM (SEQ. ID. NO: 14) |
| Pep-G2 | ANEANEANKTMPETPTGDSDP (SEQ. ID. NO: 15) |
| Pep-9 | RSVPCESNEANE (SEQ. ID. NO: 9) |
| Pep-9-Mod | RSAPCASAEVNE (SEQ. ID. NO: 13) |

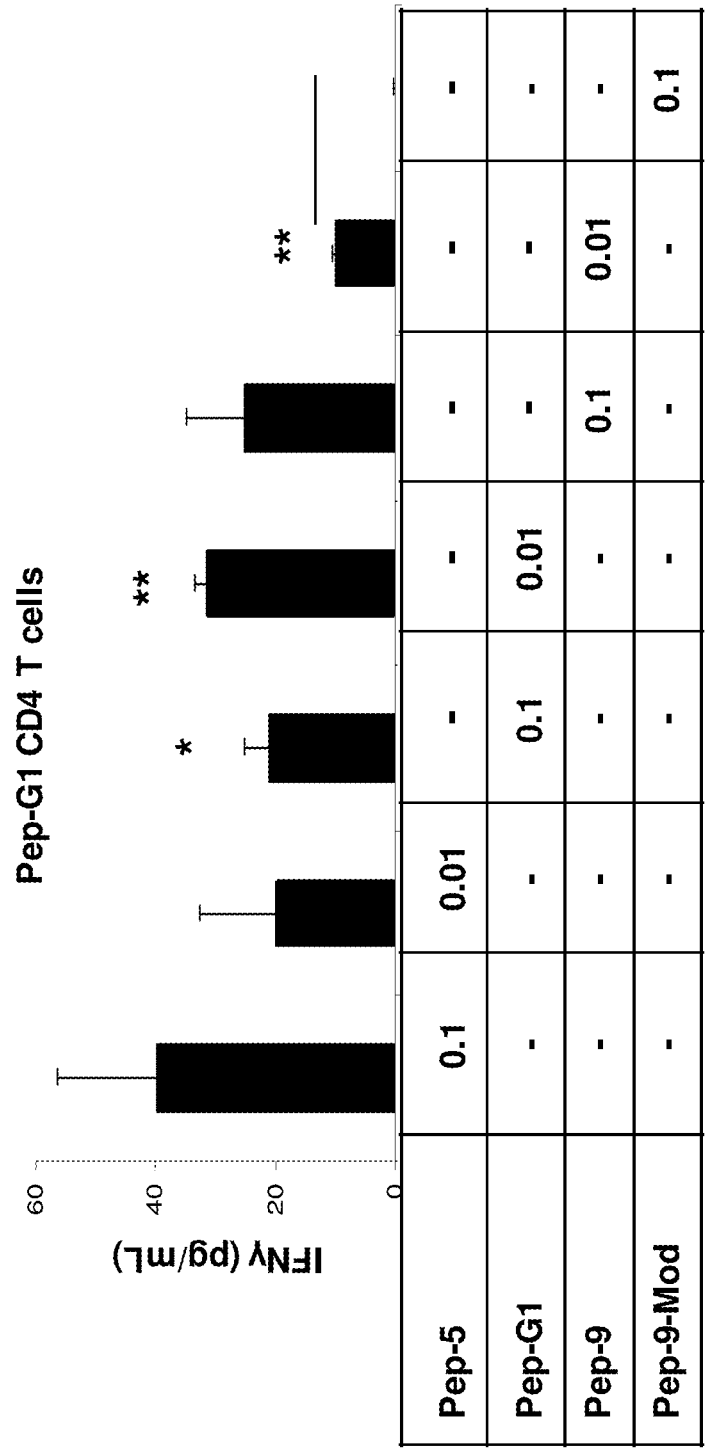

SPANX-B POLYPEPTIDES AND THEIR USE

CROSS REFERENCE TO RELATED APPLICATION

This is a divisional of U.S. patent application Ser. No. 13/203,042, filed Aug. 24, 2011, which is the §371 U.S. National Stage of International Application No. PCT/US2010/025633, filed Feb. 26, 2010, which was published in English under PCT Article 21(2), which in turn claims the benefit of U.S. Provisional Application No. 61/156,435, filed Feb. 27, 2009, both of which are incorporated by reference herein in their entirety.

FIELD

This relates to the field of cancer immunotherapy and detection, specifically to the use of SPANX-B polypeptides in the treatment and identification of cancer.

BACKGROUND

Immunotherapy involves evoking an immune response against cancer cells based on their production of target antigens. Immunotherapy based on cell-mediated immune responses involves generating a cell-mediated response to cells that produce particular antigenic determinants, while immunotherapy based on humoral immune responses involves generating specific antibodies to cells that produce particular antigenic determinants.

Recent studies show that immunotherapy of cancer patients may be dramatically improved by the finding that $CD8^+$ CTL recognize and kill tumor cells that display peptides from tumor-associated antigens within MHC Class I molecules. For example, in clinical studies it has been found that effector $CD8^+$ T cells play a major role in tumor regression. Several tumor antigens in prostate cancer models have been identified and HLA allele-specific peptides from those prostate cancer-associated antigens have been identified as $CD8^+$ T cell epitopes. For example, HLA-A2.1 binding peptides were described that were derived from prostate specific antigen (PSA) (Correale et al., *J Immunol* 161:3186, 1998), prostate-specific membrane antigen (PSMA) (Tjoa et al., *Prostate* 28:65, 1996), prostate stem cell antigen (PSCA) (Kiessling et al., *Int J Cancer* 102:390, 2002), and prostate acid phosphatase (Peshwa et al., *Prostate* 36:129, 1998). For PSA, clinical trials are in progress using different vaccine strategies.

However, there clearly is a need to identify additional antigens for use as therapeutic agents to treat other types of cancer.

SUMMARY

It is demonstrated herein that SPANX-B is widely expressed in human malignancies, particularly in melanoma and lung, colon, renal, ovarian and breast carcinomas. In melanoma specifically, its expression was associated with advanced and metastatic disease. Moreover, it is demonstrated that SPANX-B is also recognized by human T cells. Human peripheral blood contains T cell precursors that recognize SPANX-B, which can be readily expanded to generate the SPANX-B-specific $CD4^+$ and cytolytic $CD8^+$ T cells. The recognition epitopes have been mapped demonstrating that SPANX-B contains at least one immunodominant HLA-DR- and two HLA-A2-restricted epitopes. These peptides can be used to generate cytotoxic T cells that specifically lyse tumor cells expressing SPANX-B, or can be used to produce activated helper T cells.

In an embodiment, SPANX-B polypeptides are provided that are immunogenic. In several examples, the polypeptide is nine to twelve amino acids in length and includes the amino acid sequence set forth as SEQ ID NO: 1 (Pep-1), SEQ ID NO: 2 (Pep-2), SEQ ID NO: 4 (Pep-4), SEQ ID NO: 26 (modified Pep-2a), SEQ ID NO: 27 (modified Pep-1a), or SEQ ID NO: 28 (modified Pep-1b), or at least nine consecutive amino acids of SEQ ID NO: 9 (Pep-9), SEQ ID NO: 14 (Pep-G1), SEQ ID NO: 15 (Pep-G2), SEQ ID NO: 5 (Pep-5), SEQ ID NO: 7 (Pep-7), or SEQ ID NO: 8 (Pep-8). Nucleic acids encoding the polypeptides, vectors including the nucleic acids, and host cells transformed with the vectors are also provided.

In another embodiment, methods are provided for eliciting an immune response in a subject (for example, an immune response against a tumor). These methods include administering to the subject a therapeutically effective amount of a SPANX-B polypeptide, such as a polypeptide of nine to twelve amino acids in length that includes the amino acid sequence set forth as SEQ ID NO: 1, SEQ ID NO: 2, SEQ ID NO: 4, SEQ ID NO: 26, SEQ ID NO: 27, or SEQ ID NO: 28, or at least nine consecutive amino acids of SEQ ID NO: 9, SEQ ID NO: 14, SEQ ID NO: 15, SEQ ID NO: 5, SEQ ID NO: 7, or SEQ ID NO: 8. In some examples, the subject has a cancer that expresses SPANX-B.

In a further embodiment, methods are provided for activating cytotoxic T cells. These methods include contacting T cells with an effective amount of a SPANX-B polypeptide, such as a polypeptide of nine to twelve amino acids in length that includes the amino acid sequence set forth as SEQ ID NO: 1, SEQ ID NO: 2, SEQ ID NO: 4, SEQ ID NO: 26, SEQ ID NO: 27, or SEQ ID NO: 28. The cells can be in vivo or in vitro.

In another embodiment, methods are provided for producing T helper cells. These methods include contacting T cells with an effective amount of a SPANX-B polypeptide, such as a polypeptide of nine to twelve amino acids in length that includes at least nine consecutive amino acids of the amino acid sequence set forth as SEQ ID NO: 9, SEQ ID NO: 14, SEQ ID NO: 15, or SEQ ID NO: 5. The cells can be in vivo or in vitro.

The foregoing and other features of the disclosure will become more apparent from the following detailed description, which proceeds with reference to the accompanying figures.

BRIEF DESCRIPTION OF THE FIGURES

FIGS. 1A-1F are digital images, a graph and a schematic diagram illustrating the specificity of antibody and expression of SPANX-B in human immortalized tumor cell lines. FIG. 1A is a digital image showing ANEA-I0117 antibody recognized SPANX-B expressed in mouse erythroleukemia RL5 cells. Western blotting results are shown with ANEA-I0117 anti-SPANX-B antibody on lysates of RL5 cells (2 µl, 5 µl and 10 µl, respectively) transiently transduced with plasmid expressing SPANX-B (SPANX-B). Control lysates were made from untransduced parental RL5 cells (Control). FIG. 1B is a graph showing murine anti-SPANX-B antibody, which was generated from mice DNA immunized with plasmid expressing SPANX-B, recognized unique SPANX-B-specific insert of SPANX-B (encoded in Pep-G1 and Pep-2 peptides), ELISA assay on plates coated with various peptides that are depicted in FIG. 1C. FIG. 1C shows the sequence of SPANX-B (SEQ ID NO: 18) and locations of the synthetic peptides used herein. Pep-5 does not contain 6 amino acid insert of SPANX-B (underlined, SEQ ID NO: 18). FIG. 1D is a digital image showing the expression of SPANX-B protein evaluated by Western blotting with ANEA-I0117 Ab (1:5000) in lysates of cell lines, such as HEK293 (HEK), Jurkat, CRL 7002, UACC1273, 938 Mel, CCRF-CEM (CEM), and normal human donor PBMC (upper panel). The blot was stripped and hybridized with anti-actin antibody (lower panel). FIGS. 1E and 1F are digital images obtained from an immunohistochemistry and immunofluorescent assay, respectively, of melanoma (UACC1273) and ovarian carcinoma (2008 and OVCAR3) cell lines. The cells were stained with ANEA-I0117 Ab (right and bottom panels in FIG. 1E and FIG. 1F, respectively); and control IgG (left and upper panels in FIG. 1E and FIG. 1F, respectively).

FIG. 2A is a digital image of immunohistochemistry staining of slides from paraffin embedded human primary melanoma (top panel) and non-small cell lung carcinoma (NSCLC, bottom panel). Digital images of T-TMA slides with human tumors (FIG. 2B) and normal tissues (FIG. 2C) are also presented. The ANEA-I0117 antibody (SPANX-B) and control isotype-matched antibody (control IgG) were used at 1:500 dilution. FIG. 2D is a graph illustrating SPANX-B is mostly expressed in metastatic melanomas. Normalized signal intensity data for 77 genes previously identified as being associated with increased metastatic potential were averaged in each of 45 melanoma sample data sets (Mannheim data set) (Hoek et al., *Pigment Cell Res.* 19:290-3-2, 2006). This averaged profile (light shaded line) was plotted against that of SPANX-B1 (black solid line) across all samples and a positive correlation coefficient of 0.503 was calculated. Melanoma lines are labeled according to their cohort membership. Dotted lines mark the 95% confidence interval for the averaged profile. P-value is for comparisons between Cohorts A and C.

FIGS. 3A-3D are bar graphs and tables showing SPANX-B induces CD4+ T cell responses. For the results presented in FIGS. 3A and 3B, SPANX-B-specific CD4+ T cell lines were generated by repeated stimulations of human T cells with irradiated autologous immature DC treated with SPANX-B protein. The immunodominant region of SPANX-B is located in the overlapping portion of synthetic peptides Pep-G1 and Pep-5, as the T cell line can be also activated to secrete IFNγ with irradiated mature DCs pulsed with 1 µg/ml Pep-G1 or Pep-5, but not with individual peptides (Pep-G2, Pep-6) or a mixture of peptides (Pep-1, -2, -3, -4) specific to other regions of SPANX-B. The CD4+ T cell lines generated to SPANX-B protein (FIG. 3B), or Pep-5 (FIG. 3C), or Pep-G1 (FIG. 3D) specifically and reciprocally recognize DCs pulsed with titrated amounts (µg/ml) of SPANX-B protein, or Pep-5, or Pep-G1, or Pep-9 and secrete IFNγ (pg/ml). The T cells were not activated with DCs pulsed with control murine class II peptide (MOPC) or with scrambled Pep-9 (Pep-9-Mod, FIG. 3D). $P<0.01$ and *$P<0.001$ value is for comparison with the group indicated by line. The mean±SEM of representative and reproducible results of at least three independent experiments performed in triplicate are shown.

FIG. 6D shows that the CD8+ T cells did not lyse SPANX-B-negative but HLA-A2-positive OVCAR3 cells, unless pulsed with Pep-2. In FIGS. 6A-6D, the percentage of cytotoxicity (Y-axis) of a representative experiment performed in triplicate and repeated at least twice is shown. Effector CD8+ T cells also recognize and kill HLA-A2-expressing (Tc526, Tc624 and Tc2492), but not HLA-A2-negative (Tc2547 and Tc938) primary human melanoma cells (FIG. 6E). The mean±SEM (%, Y-axis) of $^{51}$Cr release of the Pep-2-specific CD8+ T cells at T:E of 1:10 are shown. Comparable cytolysis was also detected from the SPANX-B protein- and Pep-4-specific CD8+ effector cells.

SEQUENCE LISTING

Figure 1D:
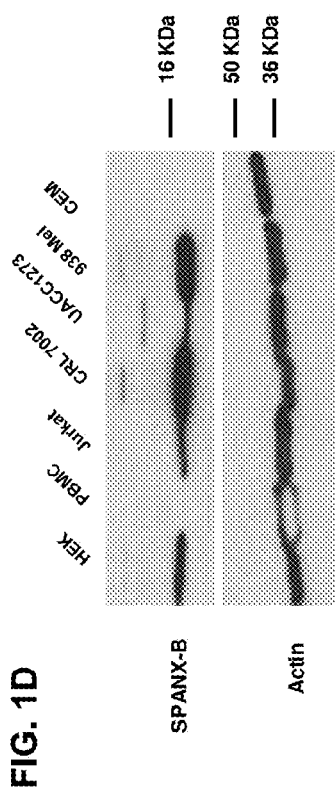

The nucleic acid and amino acid sequences listed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Jan. 13, 2014, and is 9,097 bytes, which is incorporated by reference herein.

In the accompanying sequence listing:

SEQ ID NO: 1 is the amino acid sequence of Pep-1 (SPANX-$C_{80-89}$), LQMEEEEFM

SEQ ID NO: 2 is the amino acid sequence of Pep-2 (SPANX-$B_{23-31}$), EANEANKTM.

SEQ ID NO: 3 is the amino acid sequence of Pep-3 (SPANX-$B_{2-10}$), GQQSSVRRL.

SEQ ID NO: 4 is the amino acid sequence of Pep-4 (SPANX-$B_{57-65}$), LVVRYRRNV.

SEQ ID NO: 5 is the amino acid sequence of Pep-5 (SPANX-$C_{12-35}$), RSVPCESNEVNETMPETPTGDSDP.

SEQ ID NO: 6 is the amino acid sequence of Pep-6 (SPANX-$B_{42-65}$), QPAPKKMKTSESSTILVVRYRRNV.

SEQ ID NO: 7 is the amino acid sequence of Pep-7 (SPANX-$B_{66-89}$), KRTSPEELVNDHARENRINPDQME.

SEQ ID NO: 8 is the amino acid sequence of Pep-8 (SPANX-$B_{80-103}$), ENRINPDQMEEEEFIEITTERPKK.

SEQ ID NO: 9 is the amino acid sequence of Pep-9 (SPANX-$B_{12-23}$), RSVPCESNEANE.

SEQ ID NO: 10 is the amino acid sequence of Pep-10 (SPANX-$C_{8-16}$), GGVKRSVPC.

SEQ ID NO: 11 is the amino acid sequence of Pep-11 (SPANX-$C_{86-94}$), EFMEIMVEI.

SEQ ID NO: 12 is the amino acid sequence of Pep-12 (SPANX-$BC_{43-51}$), KTSESSTIL.

SEQ ID NO: 13 is the amino acid sequence of Pep-9-Mod (SPANX-$B_{12-23}$-scrambled), RSAPCASAEVNE.

SEQ ID NO: 14 is the amino acid sequence of Pep-G1 (SPANX-$B_{11-31}$), KRSVPCESNEANEANEANKTM.

SEQ ID NO: 15 is the amino acid sequence of Pep-G2 (SPANX-$B_{21-41}$), ANEANEANKTMPETPTGDSDP.

SEQ ID NO: 16 is the amino acid sequence of MOPC (MOPC Igλ$_{91-101}$), ALWFRNHFVFGGGTK.

SEQ ID NO: 17 is the amino acid sequence of influenza HLA-A2 peptide M (Flu $M1_{58-61}$), GILGFVFTL SEQ ID NO: 18 is an exemplary amino acid sequence of SPANX-B.

SEQ ID NO: 19 is an exemplary nucleic acid sequence encoding SPANX-B.

SEQ ID NOs: 20-25 are the nucleic acid sequence of primers.

SEQ ID NO: 26 is the amino acid of modified Pep-2a, NLANEANKV.

SEQ ID NO: 27 is the amino acid sequence of modified Pep-1a, LLMEEEEFI.

SEQ ID NO: 28 is the amino acid sequence of modified Pep-1b, LQMEEEEFI.

DETAILED DESCRIPTION

It is demonstrated herein that SPANX-B is widely expressed in human malignancies, particularly in melanoma and lung, colon, renal, ovarian and breast carcinomas. In melanoma specifically, its expression was associated with advanced and metastatic disease. Moreover, it is demonstrated that SPANX-B is also recognized by human T cells and can be used for treatment.

I. Abbreviations aAPC: artificial antigen presenting cell
APC: antigen presenting cell
CTL: cytotoxic T lymphocyte
DC: dendritic cell
HLA: human major histocompatibility complex
IL-4: interleukin-4
MHC: major histocompatibility complex
NSCLC: non-small cell lung cancer
PBL: peripheral blood lymphocytes
PCR: polymerase chain reaction
PBMC: peripheral blood mononuclear cells
SPANX: sperm protein associated with the nucleus on the chromosome X
TAA: tumor associated antigen II. Terms Adjuvant: A vehicle used to enhance antigenicity; such as a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunstimulatory oligonucleotides (such as those including a CpG motif) can also be used as adjuvants (for example see U.S. Pat. Nos. 6,194,388; 6,207,646; 6,214,806; 6,218,371; 6,239,116; 6,339,068; 6,406,705; and 6,429,199).

Animal: Living multi-cellular vertebrate organisms, a category that includes, for example, mammals and birds. The term mammal includes both human and non-human mammals. Similarly, the term "subject" includes both human and veterinary subjects.

Antibody: Immunoglobulin molecules and immunologically active portions of immunoglobulin molecules, e.g., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the VL and VH domains of a single arm of an antibody, (iv) a dAb fragment (Ward et al., Nature 341:544-546, 1989) which consists of a $V_H$ domain; (v) an isolated complementarity determining region (CDR); and (vi) a F(ab')$_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faoulkner et al., Nature 298:286, 1982; Morrison, J. Immunol. 123:793, 1979; Morrison et al., Ann Rev. Immunol 2:239, 1984).

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents.

An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease-specific antigen. A tissue-specific antigen is expressed in a limited number of tissues, such as a single tissue. Specific, non-limiting examples of a tissue specific antigen are a testis specific antigen and/or a breast specific antigen. A tissue specific antigen may be expressed by more than one tissue, such as, but not limited to, an antigen that is expressed in both prostate and breast tissue. A disease-specific antigen is expressed coincidentally with a disease process. Specific non-limiting examples of a disease-specific antigen are an antigen whose expression correlates with, or is predictive of, tumor formation, such as cancer. A disease-specific antigen can be an antigen recognized by T cells or B cells.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Cancer: A malignant neoplasm that has undergone characteristic anaplasia with loss of differentiation, increased rate of growth, invasion of surrounding tissue, and is capable of metastasis. For example, prostate cancer is a malignant neoplasm that arises in or from prostate tissue, and breast cancer is a malignant neoplasm that arises in or from breast tissue (such as a ductal carcinoma). Metastatic cancer is a cancer at one or more sites in the body other than the site of origin of the original (primary) cancer from which the metastatic cancer is derived.

CD4: Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8: Cluster of differentiation factor 8, a T cell surface protein that mediates interaction with the MHC Class I molecule. Cells that express CD8 are often cytotoxic T cells.

Chemokine: A small secreted protein, induced by inflammatory stimuli. For example, it can be produced by fibroblasts, endothelial cells, epithelial cells, monocytes, macrophages, T cells, B cells, PMNs, etc. stimulated by proinflammatory cytokines such as interferon-gamma, interleukin 4, products of Th1 and Th2 lymphocytes, interleukin-1, tumor necrosis factor-alpha, and bacterial products such as lipopolysaccharide, as well as viral infection, which orchestrates a chemotactic response typically after binding to specific G-protein-coupled cell surface receptors on target cells (for example, antigen presenting cells (APC), such as dendritic cells, monocytes, macrophages, keratinocytes and B cells), that can include the selective migration, diapedesis and activation of leukocytes which mediate the inflammatory response. Four human CXC chemokine receptors (CXCR1-CXCR4), eight human CC chemokine receptors (CCR1-CCR8) and one CXXXC chemokine receptor ($CX_3CR1$) have been identified. As one example, the chemokine, interferon-induced protein 10 (IP-10) binds to the CXCR3 receptor, thus inducing chemotaxis of activated T cells, NK cells, etc., which express this receptor. As another example, the chemokine monocyte chemotactic protein-3 (MCP-3) acts via binding to the CCR1, CCR2 and CCR3 chemokine receptors on antigen presenting cells (APC) such as dendritic cells, eosinophils, basophils, monocytes and activated T cells. Thus, MCP-3 selectively targets and induces chemotaxis of these cell types.

Chemokines can include, but are not limited to, interferon-induced protein 10, monocyte chemotactic protein-3, monocyte chemotactic protein-2, monocyte chemotactic protein-1, monocyte chemotactic protein-4, macrophage inflammatory protein 1, MIP-3α, RANTES, SDF-1, MIG and macrophage-derived chemokine. Chemokines include active fragments of chemokines which retain the chemotactic activity of the intact molecule. For example, for both CC and CXC chemokines, the N terminal region is the critical region of the molecule for biological activity and leukocyte selectivity. In particular, the N-terminal ELR motif-containing CXC chemokines are chemotactic for neutrophils, whereas those not containing the motif act on lymphocytes. IP-10 and MIG, for example, do not contain the ELR motif and are known to attract activated T cells. Addition of a single amino acid residue to the amino terminus of MCP-1 decreases its biological activity up to 1000-fold and deletion of a single amino acid for that region converts the chemokine from an activator of basophils to an eosinophil chemoattractant.

Chemotherapy; chemotherapeutic agents: As used herein, any chemical agent with therapeutic usefulness in the treatment of diseases characterized by abnormal cell growth. Such diseases include tumors, neoplasms and cancer as well as diseases characterized by hyperplastic growth such as psoriasis. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g., see Slapak and Kufe, *Principles of Cancer Therapy*, Chapter 86 in Harrison's Principles of Internal Medicine, 14th edition; Perry et al., *Chemotherapy*, Ch. 17 in Abeloff, *Clinical Oncology* $2^{nd}$ ed., 2000 Churchill Livingstone, Inc; Baltzer L, Berkery R (eds): *Oncology Pocket Guide to Chemotherapy*, 2nd ed. St. Louis, Mosby-Year Book, 1995; Fischer D S, Knobf M F, Durivage H J (eds): *The Cancer Chemotherapy Handbook*, 4th ed. St. Louis, Mosby-Year Book, 1993). The immunogenic SPANX-B polypeptides disclosed herein can be used in conjunction with additional chemotherapeutic agents.

Conservative variants: "Conservative" amino acid substitutions are those substitutions that do not substantially affect or decrease an activity or antigenicity of an antigenic epitope of SPANX-B. Specific, non-limiting examples of a conservative substitution include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity.

Degenerate variant: A polynucleotide encoding an epitope of SPANX-B that includes a sequence that is degenerate as a result of the genetic code. There are 20 natural amino acids, most of which are specified by more than one codon. Therefore, all degenerate nucleotide sequences are included in this disclosure as long as the amino acid sequence of the SPANX-B polypeptide encoded by the nucleotide sequence is unchanged.

Dendritic cell (DC): Dendritic cells are the principal antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells.

Diagnostic: Identifying the presence or nature of a pathologic condition, such as, but not limited to, cancer such as melanoma, myeloma or breast cancer. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as cancer, or metastasis.

Epitope: An antigenic determinant. These are particular chemical groups or peptide sequences on a molecule that are antigenic, e.g., that elicit a specific immune response. An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996). In one embodiment, an epitope binds an MHC molecule, such an HLA molecule or a DR molecule. These molecules bind polypeptides having the correct anchor amino acids separated by about eight to about ten amino acids, such as nine amino acids.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (e.g., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like can be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques can also be used to provide for transcription of the nucleic acid sequences.

Heterologous: Originating from separate genetic sources or species. A polypeptide that is heterologous to SPANX-B originates from a nucleic acid that does not encode SPANX-B. In one specific, non-limiting example, a polypeptide comprising nine consecutive amino acids from SPANX-B and a heterologous amino acid sequence includes a β-galactosidase, a maltose binding protein, and albumin, or an immunoglobulin amino acid sequence. Generally, an antibody that specifically binds to a protein of interest will not specifically bind to a heterologous protein.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Immunogenic peptide: A peptide which comprises an allele-specific motif or other sequence such that the peptide will bind an MHC molecule and induce a cytotoxic T lymphocyte ("CTL") response, or a B cell response (e.g., antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein (e.g. HLA-A02.01) and by their ability to stimulate CD4 and/or CD8 when presented in the context of the MHC protein.

Immunogenic composition: A composition comprising an epitope of a SPANX-B polypeptide that induces a measurable CTL response against cells expressing SPANX-B polypeptide, or induces a measurable B cell response (e.g., production of antibodies that specifically bind SPANX-B) against a SPANX-B polypeptide. It further refers to isolated nucleic acids encoding an immunogenic epitope of SPANX-B polypeptide that can be used to express the epitope (and thus be used to elicit an immune response against this polypeptide). For in vitro use, the immunogenic composition can consist of the isolated nucleic acid protein or peptide. For in vivo use, the immunogenic composition will typically comprise the nucleic acid or peptide in pharmaceutically acceptable carriers, and/or other agents. A SPANX-B polypeptide, or nucleic acid encoding the polypeptide, can be readily tested for its ability to induce a CTL by art-recognized assays.

Inhibiting or treating a disease: Inhibiting a disease, such as tumor growth, refers to inhibiting the full development of a disease. In several examples, inhibiting a disease refers to lessening symptoms of a tumor, such as preventing the development of paraneoplastic syndrome in a person who is known to have cancer, or lessening a sign or symptom of the tumor. "Treatment" refers to a therapeutic intervention that ameliorates a sign or symptom of a disease or pathological condition related to the disease, such as the tumor.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes.

Linker sequence: A linker sequence is an amino acid sequence that covalently links two polypeptide domains. Linker sequences can be included in the between the SPANX-B epitopes disclosed herein to provide rotational freedom to the linked polypeptide domains and thereby to promote proper domain folding and presentation to the MHC. By way of example, in a recombinant polypeptide comprising two SPANX-B domains, linker sequences can be provided between them. Linker sequences, which are generally between 2 and 25 amino acids in length, are well known in the art and include, but are not limited to, the glycine(4)-serine spacer (GGGGS×3) described by Chaudhary et al., *Nature* 339:394-397, 1989.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Neoplasm: An abnormal cellular proliferation, which includes benign and malignant tumors, as well as other proliferative disorders.

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Peptide: A chain of amino acids of between 3 and 30 amino acids in length. In one embodiment, a peptide is from about 7 to about 25 amino acids in length. In yet another embodiment, a peptide is from about 9 to about 12 amino acids in length, such as about 8 to about 10 amino acids in length. In yet another embodiment, a peptide is about 9 amino acids in length.

Peptide Modifications: SPANX-B epitopes include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an immunogenic SPANX-B polypeptide having measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology*, Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition (1995), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a chemical composition or a cell to achieve a desired effect in a subject being treated. For instance, this can be the amount necessary to inhibit tumor growth or to measurably alter outward symptoms of the tumor. When administered to a subject, a dosage will generally be used that will achieve target tissue concentrations (for example, in lymphocytes) that has been shown to achieve an in vitro effect.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (e.g., glycosylation or phosphorylation). In one embodiment, the polypeptide is a SPANX-B polypeptide.

Probes and primers: A probe comprises an isolated nucleic acid attached to a detectable label or reporter molecule. Primers are short nucleic acids, preferably DNA oligonucleotides, of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example by polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers can be selected that comprise about 20, 25, 30, 35, 40, 50 or more consecutive nucleotides.

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques can also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Protein Purification: The epitopes of SPANX-B disclosed herein can be purified (and/or synthesized) by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982). Substantial purification denotes purification from other proteins or cellular components. A substantially purified protein is at least about 60%, 70%, 80%, 90%, 95%, 98% or 99% pure. Thus, in one specific, non-limiting example, a substantially purified protein is 90% free of other proteins or cellular components.

Purified: The term purified does not require absolute purity; rather, it is intended as a relative term. Thus, for example, a purified nucleic acid is one in which the nucleic acid is more enriched than the nucleic acid in its natural environment within a cell. Similarly, a purified peptide preparation is one in which the peptide or protein is more enriched than the peptide or protein is in its natural environment within a cell. In one embodiment, a preparation is purified such that the protein or peptide represents at least about 60% (such as, but not limited to, 70%, 80%, 90%, 95%, 98% or 99%) of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA versus DNA) of the hybridizing regions of the nucleic acids can be considered in selecting hybridization conditions. An additional consideration is whether one of the nucleic acids is immobilized, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2× SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual,* 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between nucleic acid or amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a SPANX-B polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a SPANX-B polypeptide are typically characterized by possession of at least 75%, for example at least 80%, sequence identity counted over the full length alignment with the amino acid sequence of SPANX-B using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and can possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

SPANX (sperm protein associated with the nucleus on the chromosome X): a family of highly homologous proteins that share about 40-50% similarity with each other. SPANX is encoded by an ancestral SPANX-N and its descendant SPANX-A/D genes (Kourpina et al., *Proc Natl Acad Sci USA* 101(9):3077-82, 2004) that contain two exons separated by a 650 bp intron with an inserted retroviral LTR sequence (Zendman et al., *Gene* 309(2):125-33, 2003). SPANX-A/D has five members (SPANX-A1, -A2, -B, -C, and -D) classified on the basis of diagnostic amino acid substitutions. The SPANX-A1, -C, and -D genes encode 97 amino acid proteins; while the SPANX-B gene, which can have up to a dozen copies, expresses a 103 amino acid protein (Kouprina et al., *Genome Res* 15(11):1477-86, 2005). Many members of the SPANX family are not expressed in nongametogenic adult tissues. These proteins have a unique expression and localization in specific subpopulations of spermatids and spermatozoa (Westbrook et al., *Mol Hum Reprod* 12(11):703-16, 2006). Thus, SPANX proteins are believed to participate in mammalian spermatogenesis. SPANX-A and SPANX-B are localized in nuclear craters and cytoplasmic droplets of ejaculated spermatozoa, respectively (Westbrook et al., *Biol Reprod* 64(1): 345-58, 2001).

SPANX is a typical cancer-testis (CT) antigen, since SPANX genes are also specifically expressed in variety of human tumors and in normal testis (see, for example, Zendman et al., *Cancer Res* 59(24):6223-9, 1999). SPANX-B, as well as members (SPANX-A1, -A2, and -C) have been shown to be expressed in melanoma, bladder carcinomas, hematological malignancies and myeloma, amongst other tumors (see, for example, Wang et al., *Blood* 101(3):955-60, 2003; Westbrook et al., *Clin Cancer Res* 10(1 Pt 1):101-12, 2004). SPANX-positivity may also indicate the presence of more aggressive skin tumors, particularly in distant, nonlymphatic metastatic melanomas (Westbrook et al., *Clin Cancer Res* 10(1 Pt 1):101-12, 2004). In addition, sera of cancer patients contained high titers of SPANX antibody (Westbrook et al., op. cit.).

Subject: Living multi-cellular vertebrate organisms, a category that includes both human and veterinary subjects, including human and non-human mammals.

T cell: A white blood cell critical to the immune response. T cells include, but are not limited to, CD4+ T cells and CD8+ T cells. A CD4+ T lymphocyte is an immune cell that carries a marker on its surface known as "cluster of differentiation 4" (CD4). These cells, also known as helper T cells, help orchestrate the immune response, including antibody responses as well as killer T cell responses. CD8+ T cells carry the "cluster of differentiation 8" (CD8) marker. In one embodiment, a CD8 T cell is a cytotoxic T lymphocyte. In another embodiment, a CD8 cell is a suppressor T cell.

Therapeutically active polypeptide: An agent, such as an epitope of SPANX-B that causes induction of an immune response, as measured by clinical response (for example increase in a population of immune cells, increased cytolytic activity against cells that express SPANX-B, or measurable reduction of tumor burden). Therapeutically active molecules can also be made from nucleic acids. Examples of a nucleic acid based therapeutically active molecule is a nucleic acid sequence that encodes a SPANX-B epitope, wherein the nucleic acid sequence is operably linked to a control element such as a promoter.

In one embodiment, a therapeutically effective amount of an epitope of SPANX-B is an amount used to generate an immune response, or to treat cancer in a subject. Specific, non-limiting examples are a polypeptide having a sequence set forth as SEQ ID NOs: 1-15 and 26-28. Treatment refers to a therapeutic intervention that ameliorates a sign or symptom of cancer, or a reduction in tumor burden.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Immunogenic SPANX-B Peptides

Methods are provided herein for treating cancer. These methods utilize SPANX-B polypeptides. An exemplary SPANX-B amino acid sequence is set forth below:

```
                                       (SEQ ID NO: 18)
MGQQSSVRRL KRSVPCESNE ANEANEANKT MPETPTGDSD

PQPAPKKMKT SESSTILVVR YRRNVKRTSP EELLNDHARE

NRINPDQMEE EEFIEITTER PKK,
``` see also GENBANK® Accession No. AAW47383, AAW47382 and AAW47380, all dated Nov. 5, 2005; all herein incorporated by reference. In other embodiments, SPANX-B has an amino acid sequence at least 90% identical to SEQ ID NO: 18, for example a polypeptide that has at least about 91%, 92%, 93%, 94%, 95%, 96%, 97%, 98% or 99% sequence identity to SEQ ID NO: 18.

Using the genetic code, one of skill in the art can readily produce a nucleic acid sequence encoding SPANX-B. In one example, SPANX-B is encoded by a nucleic acid having a sequence set forth as:

```
                                                           (SEQ ID NO: 19)
AGGGTGTGGC TTTGCCTTGT CACCAGGAGG GTATGCATAG GGAGGGCAAG AGCTCTGGGC

CACTGCGAAG ATTCAAAAGC TCCAAAAACC TACTGTAGAC ATCGAAGAAC CAATATATAC

AATGGGCCAA CAATCCAGTG TCCGCAGGCT GAAGAGGAGC GTCCCCTGTG AATCCAACGA

GGCCAACGAG GCCAATGAGG CCAACAAGAC GGTAAGATTG TTAGGTTTTG AAGTGAAGGC

GAGGGTGAAA GAAAGACACA CAGAGCGGGG GCGGCTCAAA CAACAACACA GGAATATTGC

GGGTGCTTGT AGGTAGGGGT GGGAGGGGCC TGGGCAGTAT GGCTTGCTGC CCGGCAGGAT

ATTGATAAGA TGTTCTTATG ATCAGGTGGT TTGGCCCTTT TTCTGGTGGA ATATCATTGT

GGTGTTCCTT AGAACGCTGC CAAGCAAGAT ATGATAGGGA TGTTTCTTCA GTTGGGCCTT

TGTCCGCCTT GCGGACAGGT GGTTAGGCAG GATGTTTCTC ACGGCCTGAA CCCCCATGGG

ATGTTTCACT TTGACCAAGG TCTGCAAAAT AGCAAAGAAC TGACAAAATG GTGCAGTTTG

GACTCACAGG TGACCCTACC CACGCTCCTC TTCTTCTTCC CCATAGATCC CTACTCTGTG
```

```
                                -continued
CTTCAACCTT CTTCTTCTCT GGATCAAACC CCTTCCTCAA CCTGCATTCC TTCTTCTCAT

GAAGCCCCCT TTGCTATCCA GTCTCTATCC TGTTCACCCA AAATAATGTC CTCCTGGCCT

CTCCCTGCTT TCTTAACAGA TGCCGGAGAC CCCAACTGGG GACTCAGACC CGCAACCTGC

TCCTAAAAAA ATGAAAACAT CTGAGTCCTC GACCATACTA GTGGTTCGCT ACAGGAGGAA

CGTGAAAAGA ACATCTCCAG AGGAACTGCT GAATGACCAC GCCCGAGAGA ACAGAATCAA

CCCCGACCAA ATGGAGGAGG AGGAATTCAT AGAAATAACG ACTGAAAGAC CTAAAAAGTA

GCAAGAAGCT ACATCCCTCA AACTTCGGCA ATGAAAATAA AGTTTGAGAA GCTGATGGCT

GTGTATATCT CTGCCTGTTT TCTGATGGGG GGGGT,
``` see also GENBANK® Accession No. AY787632, Nov. 5, 2005; incorporated herein by reference. In other embodiments, a nucleic acid sequence encoding SPANX-B has a nucleic acid sequence at least 90% identical to SEQ ID NO: 19, for example a polynucleotide that has at least about 91%, 92%, 93%, 94%, 95%, 96%, 97%, 98% or 99% sequence identity to SEQ ID NO: 19.

Immunogenic fragments of SPANX-B (and SPANX-B itself), can be chemically synthesized by standard methods. If desired, polypeptides can also be chemically synthesized by emerging technologies. One such process is described in Lu et al., *FEBS Lett.* 429:31-35, 1998. Polypeptides can also be produced using molecular genetic techniques, such as by inserting a nucleic acid encoding SPANX-B or an epitope thereof into an expression vector, introducing the expression vector into a host cell, and isolating the polypeptide.

SPANX-B polypeptides are disclosed herein that can be used to induce an immune response (are immunogenic, for example, induce an immune response against a tumor). These peptides are nine to twelve amino acids, such as eleven, ten, or nine consecutive amino acids of a SPANX-B polypeptide. In some embodiments, an immunogenic SPANX-B polypeptide is nine to twelve amino acids in length and includes, or consists of, the amino acid sequence set forth as SEQ ID NO: 1, the amino acid sequence set forth as SEQ ID NO: 2, or the amino acid sequence set forth as SEQ ID NO: 4. The immunogenic SPANX-B polypeptide can also be nine to twelve amino acids in length and include, or consist of, the amino acid sequence set forth as SEQ ID NO: 1 with a single conservative amino acid substitution, the amino acid sequence set forth as SEQ ID NO: 2 with a single conservative amino acid substitution, or the amino acid sequence set forth as SEQ ID NO: 4 with a single conservative substitution thereof.

In some embodiments, an immunogenic SPANX-B polypeptide is nine to twelve amino acid in length and includes or consists of the amino acid sequence set forth as NLANEANKV (SEQ ID NO: 26), LLMEEEEFI (SEQ ID NO: 27), or LQMEEEEFI (SEQ ID NO: 28). The immunogenic SPANX-B polypeptide can also be nine to twelve amino acid in length and include or consist of the amino acid sequence set forth as SEQ ID NO: 26 with a single conservative amino acid substitution, SEQ ID NO: 27 with a single conservative amino acid substitution, or SEQ ID NO: 28 with a single conservative amino acid substitution.

In other embodiments, an immunogenic SPANX-B polypeptide includes, or consists of, nine to twelve amino acids of SEQ ID NO: 5, SEQ ID NO: 7, SEQ ID NO: 8, SEQ ID NO: 9, SEQ ID NO: 14, or SEQ ID NO: 15. In further embodiments, an immunogenic SPANX-B polypeptide is nine to twelve amino acids in length and includes, or consists of, SEQ ID NO: 5 with a single conservative amino acid substitution, SEQ ID NO: 7 with a single conservative amino acid substitution, SEQ ID NO: 8 with a single conservative amino acid substitution, SEQ ID NO: 9 with a single conservative amino acid substitution, SEQ ID NO: 14 with a single conservative amino acid substitution, or SEQ ID NO: 15 with a single conservative amino acid substitution.

Generally, the immunogenic polypeptides disclosed herein do not include the amino acid sequence set forth as SEQ ID NO: 18 (SPANX-B).

In several embodiments, the isolated SPANX-B polypeptide is included in a fusion protein. Thus, the fusion protein can include the SPANX-B polypeptide (see above) and a second heterologous moiety, such as a myc protein, an enzyme or a carrier (such as a hepatitis carrier protein or bovine serum albumin) covalently linked to the SPANX-B polypeptide. Thus, a second heterologous moiety is non-covalently linked to the SPANX-B polypeptide.

These above-described SPANX-B polypeptides are immunogenic, and thus can be used to induce an immune response in a subject. In some examples, the SPANX-B polypeptides induce an immune response against a tumor in a subject. In some embodiments, the SPANX-B polypeptides disclosed herein do not include additional consecutive amino acids of SEQ ID NO: 18.

The above-described SPANX-B polypeptides can be included in a fusion protein with a chemokine. The chemokine can be interferon-induced protein (IP) 10, monocyte chemotactic protein (MCP)-3, MCP-2, MCP-1, MCP-4, macrophage inflammatory protein (MIP)-1, MIP-3α (CCL20), RANTES, SDF-1, MIG, or macrophage-derived chemokine (MDC/CCL22). See, e.g., U.S. Pat. No. 6,562,347, herein incorporated by reference. In other examples, the SPANX-B polypeptides can be included in a fusion protein with a defensin (such as a β-defensin, for example, β-defensin 2 or β-defensin 3). See, e.g., U.S. Pat. Publication No. 2005/0095257, incorporated herein by reference. In another example, the SPANX-B polypeptides can be included in a fusion protein with Hsp70 (for example, mycobacterial Hsp70).

Without being bound by theory, it is believed that the presentation of peptides by MHC molecules involves binding through the anchor residues of the peptide and ultimate presentation on the cell surface. The polypeptides disclosed herein are presented by MHC Class I or MHC Class II. MHC Class I molecules present epitopes from endogenous proteins for presentation to CTL cells. HLA A, HLA B and HLA C molecules bind peptides of about eight to ten amino acids in length (such as nine amino acids in length) that have particular anchoring residues. The anchoring residues recognized by an HLA Class I molecule depend upon the particular allelic form of the HLA molecule. A $CD8^+$ T cell bears T cell receptors that recognize a specific epitope when presented by a particular HLA molecule on a cell. When a CTL precursor that has been stimulated by an antigen presenting cell to become a cytotoxic T lymphocyte contacts a cell that bears such an HLA-peptide complex, the CTL forms a conjugate with the cell and destroys it. In several examples presented herein, the polypeptides that are disclosed bind and are presented by HLA-A2.1. In some embodiments, the polypeptide can consist of the amino acid sequence set forth as one of SEQ ID NO: 1, SEQ ID NO: 2, SEQ ID NO: 4, SEQ ID NO: 26, SEQ ID NO: 27, SEQ ID NO: 28, SEQ ID NO: 1 with a single conservative amino acid substitution, SEQ ID NO: 2 with a single conservative amino acid substitution, SEQ ID NO: 4 with a single conservative amino acid substitution, SEQ ID NO: 26 with a single conservative amino acid substitution, SEQ ID NO: 27 with a single conservative amino acid substitution, or SEQ ID NO: 28 with a single conservative amino acid substitution.

MHC Class II molecules present epitopes from endogenous proteins for presentation to T helper cells. HLA-DR is a major histocompatibility complex, MHC class II, cell surface receptor encoded by the human leukocyte antigen complex on chromosome 6 region 6p21.31. The complex of HLA-DR and its ligand, a peptide of 9 amino acids in length or longer, constitutes a ligand for the T-cell receptor (TCR). In some embodiments the SPANX-B polypeptides disclosed herein bind MHC Class II, such as a polypeptide consisting of at least 9 amino acids of SEQ ID NO: 5, SEQ ID NO: 9, SEQ ID NO: 14, SEQ ID NO: 15, SEQ ID NO: 5 with a single conservative amino acid substitution, SEQ ID NO: 9 with a single conservative amino acid substitution, SEQ ID NO: 14 with a single amino acid substitution, or SEQ ID NO: 15 with a single conservative amino acid substitution.

Peptides that bind well are usually "dominant" epitopes, while those that bind less well are often "subdominant" or "cryptic" epitopes. Dominant epitopes of either self proteins or foreign proteins evoke strong immune responses. Subdominant or cryptic epitopes generate weak responses or no responses at all. Without being bound by theory, tighter binding by dominant epitopes to MHC molecules results in their denser presentation on the cell surface, greater opportunity to react with immune cells and greater likelihood of eliciting an immune response or tolerance.

In several examples, the SPANX-B polypeptide can be repeated in series, such that the polypeptide includes several copies of the immunogenic SPANX-B polypeptide. However, only one copy of the SPANX-B polypeptide can be included in an immunogenic molecule. In several examples, two, three, four, or five copies of the SPANX-B polypeptide are included in an immunogenic molecule. The copies of the SPANX-B polypeptide can be separated by peptide linkers.

In additional examples, the polypeptide can be a fusion protein and can also include heterologous sequences to SPANX-B (such as amino acid sequences of at least nine amino acids in length that are not included in SEQ ID NO: 18). Thus, in several specific non-limiting examples, the immunogenic peptide is a fusion polypeptide, for example the polypeptide includes six sequential histidine residues, a β-galactosidase amino acid sequence, an immunoglobulin amino acid sequence, a chemokine amino acid sequence, a defensin amino acid sequence, or a Hsp70 amino acid sequence. As noted above, the fusion polypeptide can optionally include repetitions of one or more of the SPANX-B polypeptides disclosed herein, such as two, three, four, five, or up to ten repetitions of one of a SPANX-B polypeptide. A linker sequence can optionally be included between the SPANX-B polypeptides. In all of these examples, the polypeptide does not include the full-length SPANX-B amino acid sequence, such as the amino acid sequence set forth as SEQ ID NO: 18.

The SPANX-B polypeptides disclosed herein can be chemically synthesized by standard methods, or can be produced recombinantly. An exemplary process for polypeptide production is described in Lu et al., *FEBS Lett.* 429:31-35, 1998. They can also be isolated by methods including preparative chromatography and immunological separations.

A SPANX-B polypeptide can be covalently linked to a carrier, which is an immunogenic macromolecule to which an antigenic molecule can be bound. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)). Suitable carriers include, but are not limited to, a hepatitis B small envelope protein HBsAg. This protein has the capacity to self assemble into aggregates and can form viral-like particles. The preparation of HBsAg is well documented, see for example European Patent Application Publication No. EP-A-0 226 846, European Patent Application Publication No. EP-A-0 299 108 and PCT Publication No. WO 01/117554, and the amino acid sequence disclosed, for example, in Tiollais et al., *Nature*, 317: 489, 1985, and European Patent Publication No. EP-A-0 278 940, and PCT Publication No. WO 91/14703, all of which are incorporated herein by reference.

Polynucleotides encoding the SPANX-B polypeptides disclosed herein are also provided. These polynucleotides include DNA, cDNA and RNA sequences which encode the polypeptide of interest. Silent mutations in the coding sequence result from the degeneracy (redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, *Biochemistry*, 3rd Edition, W.H. Freeman and Co., NY).

A nucleic acid encoding a SPANX-B polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to per-sons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding a SPANX-B polypeptide include a recombinant DNA which is incorporated into a vector in an autonomously replicating plasmid or virus or into the genomic DNA of a prokaryote or eukaryote, or which exists as a separate molecule (such as a cDNA) independent of other sequences. The polynucleotide can also include a recombinant DNA encoding a SPANX-B polypeptide linked to a heterologous DNA encoding for example, a chemokine (for example, IP-10, MCP-3, MCP-2, MCP-1, MCP-4, MIP-1, MIP-3α (CCL20), RANTES, SDF-1, MIG, or MDC/CCL22), a defensin (for example, β-defensin 2 or β-defensin 3) or Hsp70.

In one embodiment, vectors are used for expression in yeast such as *S. cerevisiae* or *Kluyveromyces lactis*. Several promoters are known to be of use in yeast expression systems such as the constitutive promoters plasma membrane H$^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2 μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The SPANX-B peptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase, which controls the activation of other vacuolar hydrolases. Heterologous expression in strains carrying temperature-sensitive (ts) alleles of genes can be employed if the corresponding null mutant is inviable.

Viral vectors can also be prepared encoding the SPANX-B polypeptides disclosed herein. A number of viral vectors have been constructed, including polyoma, SV40 (Madzak et al., 1992, *J. Gen. Virol.*, 73:15331536), adenovirus (Berkner, 1992, *Cur. Top. Microbiol. Immunol.*, 158:39-6; Berliner et al., 1988, *BioTechniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV (Margolskee, 1992, *Curr. Top. Microbiol. Immunol.*, 158:67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (Herweijer et al., 1995, *Human Gene Therapy* 6:1161-1167; U.S. Pat. Nos. 5,091,309 and 5,2217,879), alphaviruses (Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (Autographa californica multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding a SPANX-B polypeptide is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Pox viruses useful in practicing the present invention include orthopox, suipox, avipox, and capripox virus. Orthopox includes vaccinia, ectromelia, and raccoon pox. One example of an orthopox of use is vaccinia. Avipox includes fowlpox, canary pox and pigeon pox. Capripox includes goat pox and sheep pox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and polio.

In some cases, vaccinia viral vectors may elicit a strong antibody response. Thus, while numerous boosts with vaccinia vectors are possible, its repeated use may not be useful in certain instances. However, this sensitivity problem can be minimized by using pox from different genera for boosts. In one example, when the first or initial pox virus vector is vaccinia, the second and subsequent pox virus vectors are selected from the pox viruses from a different genus such as suipox, avipox, capripox or an orthopox immunogenically distinct from vaccinia.

The vaccinia virus genome is known in the art. It is composed of a HIND F13L region, TK region, and an HA region. Recombinant vaccinia virus has been used to incorporate an exogenous gene for expression of the exogenous gene product (see, for example, Perkus et al., *Science* 229:981-984, 1985; Kaufman et al., *Int. J. Cancer* 48:900-907, 1991; Moss, *Science* 252:1662, 1991). A gene encoding an antigen of interest, such as an immunogenic SPANX-B polypeptide, can be incorporated into the HIND F13L region or alternatively incorporated into the TK region of recombinant vaccinia virus vector (or other nonessential regions of the vaccinia virus genome). Baxby and Paoletti (*Vaccine* 10:8-9, 1992) disclose the construction and use as a vector, of the non-replicating poxvirus, including canarypox virus, fowlpox virus and other avian species. Sutter and Moss (*Proc. Natl. Acad. Sci USA* 89:10847-10851, 1992) and Sutter et al. (*Virology* 1994) disclose the construction and use as a vector, the non-replicating recombinant Ankara virus (MVA, modified vaccinia Ankara) in the construction and use of a vector.

Suitable vectors are disclosed, for example, in U.S. Pat. No. 6,998,252, which is incorporated herein by reference. In one example, a recombinant poxvirus, such as a recombinant vaccinia virus is synthetically modified by insertion of a chimeric gene containing vaccinia regulatory sequences or DNA sequences functionally equivalent thereto flanking DNA sequences which in nature are not contiguous with the flanking vaccinia regulatory DNA sequences that encode a SPANX-B polypeptide. The recombinant virus containing such a chimeric gene is effective at expressing the SPANX-B polypeptide. In one example, the vaccine viral vector comprises (A) a segment comprised of (i) a first DNA sequence encoding a SPANX-B polypeptide and (ii) a poxvirus promoter, wherein the poxvirus promoter is adjacent to and exerts transcriptional control over the DNA sequence encoding a SPANX-B polypeptide; and, flanking said segment, (B) DNA from a nonessential region of a poxvirus genome. The viral vector can encode a selectable marker. In one example, the poxvirus includes, for example, a thymidine kinase gene (see U.S. Pat. No. 6,998,252, which is incorporated herein by reference).

Examples of expression control elements of use in these vectors include, but are not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the SPANX-B polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al. in *Current Protocols in Molecular Biology*, John Wiley and Sons, New York, N.Y., 1987) and are commercially available. Generally, a DNA donor vector contains the following elements: (i) a prokaryotic origin of replication, so that the vector may be amplified in a prokaryotic host; (ii) a gene encoding a marker which allows selection of prokaryotic host cells that contain the vector (e.g., a gene encoding antibiotic resistance); (iii) at least one DNA sequence encoding a SPANX-B polypeptide located adjacent to a transcriptional promoter capable of directing the expression of the sequence; and (iv) DNA sequences homologous to the region of the parent virus genome where the foreign gene(s) will be inserted, flanking the construct of element (iii). Methods for constructing donor plasmids for the introduction of multiple foreign genes into pox virus are described in PCT Publication No. WO 91/19803.

Basic techniques for preparing recombinant DNA viruses containing a heterologous DNA sequence encoding the SPANX-B polypeptide are known in the art. Such techniques involve, for example, homologous recombination between the viral DNA sequences flanking the DNA sequence in a donor plasmid and homologous sequences present in the parental virus (Mackett et al., 1982, *Proc. Natl. Acad. Sci. USA* 79:7415-7419). The vector can be constructed for example by steps known in the art, such as steps analogous to the methods for creating synthetic recombinants of the fowlpox virus described in U.S. Pat. No. 5,093,258. Other techniques include using a unique restriction endonuclease site that is naturally present or artificially inserted in the parental viral vector to insert the heterologous DNA.

Generally, DNA fragments for construction of the donor vector, including fragments containing transcriptional promoters and fragments containing sequences homologous to the region of the parent virus genome into which foreign DNA sequences are to be inserted, can be obtained from genomic DNA or cloned DNA fragments. The donor plasmids can be mono, di-, or multivalent (e.g., can contain one or more inserted foreign DNA sequences). The donor vector can contain an additional gene that encodes a marker that will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., 1988, *J. Virol.* 62:1046; Falkner and Moss, 1988, *J. Virol.* 62:1849; Franke et al., 1985, *Mol. Cell. Biol.* 5:1918), as well as genes such as the *E. coli* lacZ gene, that permit identification of recombinant viral plaques by colorimetric assay (Panicali et al., 1986, *Gene* 47:193-199).

The DNA gene sequence to be inserted into the virus can be placed into a donor plasmid, such as an *E. coli* or a *Salmonella* plasmid construct, into which DNA homologous to a section of DNA such as that of the insertion site of the poxvirus where the DNA is to be inserted has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA that is the desired insertion region. With a parental pox viral vector, a pox promoter is used. The resulting plasmid construct is then amplified by growth within *E. coli* bacteria and isolated. Next, the isolated plasmid containing the DNA gene sequence to be inserted is transfected into a cell culture, for example chick embryo fibroblasts, along with the parental virus, for example poxvirus. Recombination between homologous pox DNA in the plasmid and the viral genome respectively results in a recombinant poxvirus modified by the presence of the promoter-gene construct in its genome, at a site that does not affect virus viability.

As noted above, the DNA sequence is inserted into a region (insertion region) in the virus that does not affect virus viability of the resultant recombinant virus. One of skill in the art can readily identify such regions in a virus by, for example, randomly testing segments of virus DNA for regions that allow recombinant formation without seriously affecting virus viability of the recombinant. One region that can readily be used and is present in many viruses is the thymidine kinase (TK) gene. The TK gene has been found in all pox virus genomes examined, including leporipoxvirus (Upton et al., 1986, *J. Virology* 60:920); shope fibromavirus; capripoxvirus (Gershon et al., 1989, *J. Gen. Virol.* 70:525) Kenya sheep-1; orthopoxvirus (Weir et al., 1983, *J. Virol.* 46:530) vaccinia (Esposito et al., 1984, *Virology* 135:561); monkeypox and variola virus (Hruby et al., 1983, *Proc. Natl. Acad. Sci. USA* 80:3411) vaccinia (Kilpatrick et al., 1985, *Virology* 143:399); Yaba monkey tumor virus; avipoxvirus (Binns et al., 1988, *J.*

Gen. Virol. 69:1275); fowlpox; (Boyle et al., 1987, Virology 156:355); fowlpox, quailpox (Schnitzlein et al., 1988, J. Virological Methods 20:341); entomopoxvirus (Lytvyn et al., 1992, J. Gen. Virol. 73:3235-3240). In vaccinia, in addition to the TK region, other insertion regions include, for example, the HindIII M fragment. In fowlpox, in addition to the TK region, other insertion regions include, for example, the BamHI J fragment (Jenkins et al., 1991, AIDS Res Hum Retroviruses 7:991-998) the EcoRI-HindIII fragment, EcoRV-HindIII fragment, BamHI fragment and the HindIII fragment set forth in EPO Application No. 0 308220 A1 (see also Calvert et al., 1993, J. Virol. 67:3069-3076; Taylor et al., 1988, Vaccine 6:497-503; Spehner et al., 1990; Boursnell et al., 1990, J. Gen. Virol. 71:621-628).

Homologous recombination between donor plasmid DNA and viral DNA in an infected cell can result in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (see U.S. Pat. No. 4,603,112 and PCT Publication No. WO 89/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK- and can be selected on this basis (Mackett et al., 1982, Proc. Natl. Acad. Sci. USA 79:7415). Alternatively, co-integration of a gene encoding a marker or indicator gene with the foreign gene(s) of interest, as described above, can be used to identify recombinant progeny. One specific non-limiting example of an indicator gene is the E. coli lacZ gene. Recombinant viruses expressing beta-galactosidase can be selected using a chromogenic substrate for the enzyme (Panicali et al., 1986, Gene 47:193). Once a recombinant virus has been identified, a variety of well-known methods can be used to assay the expression of the SPANX-B sequence encoded by the inserted DNA fragment. These methods include black plaque assay (an in situ enzyme immunoassay performed on viral plaques), Western blot analysis, radioimmunoprecipitation (RIPA), and enzyme immunoassay (EIA).

This disclosure encompasses a recombinant virus comprising more than one antigen of interest for the purpose of having a multivalent vaccine. For example, the recombinant virus may comprise the virus genome or portions thereof, the nucleic acid sequence encoding the SPANX-B polypeptide and a nucleic acid sequence encoding a hepatitis B surface antigen.

In one embodiment, a composition is provided that includes a recombinant virus comprising a vaccinia virus genome or portions thereof, the nucleic acid sequence encoding a SPANX-B polypeptide and a recombinant virus comprising the nucleic acid sequence encoding the immunostimulatory molecule B7-1, alone or in combination with the nucleic acid sequence encoding the immunostimulatory molecule B7-2, or a recombinant virus containing both the genes for a tumor antigen and an immunostimulatory molecule. This disclosure also encompasses a recombinant virus comprising the SPANX-B polypeptide that is administered with a second recombinant virus comprising the virus genome or portion thereof, and one or more nucleic acid sequences encoding one or more B7 molecules, such as a recombinant vaccinia virus expressing B7-1 and/or B7-2. It is disclosed in U.S. Pat. No. 6,893,869 that the rapid infection of tumor cells with these recombinant viruses demonstrates that vaccinia can authentically express these proteins and that they are functional molecules. Following transfer of the nucleic acids, weakly immunogenic syngeneic tumors expressing these recombinant molecules are rejected by immunocompetent hosts.

Thus, in one example, recombinant virus is disclosed that is a recombinant vaccinia virus containing B7-1 and a recombinant vaccinia virus containing B7-2 (designated rV-B7-1 and rV-B7-2, respectively); the composition can include rV-B7-1 and/or rV-B7-2 in combination with an immunogenic SPANX-B polypeptide.

The B7 molecule includes but is not limited to B7-1, B7-2 and analogs thereof. The B7 gene may be cloned from mammalian sources, including but not limited to mammalian tissues, genomic libraries or cDNA libraries, such as from murine or human sources. Without being bound by theory, co-stimulatory molecules of the B7 family (namely B7-1, B7-2, and possibly B7-3) are believed to be members of the immunoglobulin gene superfamily. These molecules are present on macrophages, dendritic cells, monocytes (antigen presenting cells (APCs)). Significant amplification of the immune response against a given antigen generally does not occur without co-stimulation (June et al., Immunology Today 15:321-331, 1994; Chen et al. Immunology Today 14:483-486, 1993; Townsend et al. Science 259:368-370, 1993). Freeman et al. (J. Immunol. 143:2714-2722, 1989) report cloning and sequencing of B7-1 gene; Azuma et al. (Nature 366:76-79, 1993) report cloning and sequencing B7-2 gene. Thus, in one embodiment the B7-1 gene or the B7-2 genes are administered in conjunction with the SPANX-B polypeptide. The insertion of nucleic acids encoding B7-1 and B7-2 into vaccinia virus has been disclosed (see for example, U.S. Pat. No. 6,893,869, incorporated herein by reference; this U.S. patent also discloses the use of a nucleic acid encoding IL-2 in a vaccinia virus). Several vectors including IL-2, B7-1 and B7-2 have been deposited with the American Type Culture Collection (ATCC) on Oct. 3, 1994 under the terms of the Budapest Treaty (for example, rV-CEA/$_n$IL-2 (ATCC Designation VR 2480), rV-$_m$B7-2 (ATCC Designation VR 2482); and rV-$_m$B7-1 (ATCC Designation VR 2483).

DNA sequences encoding a SPANX-B polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include Escherichia coli, Bacillus subtilis, Saccharomyces cerevisiae, Salmonella typhimurium, SF9 cells, C129 cells, 293 cells, Neurospora, and immortalized mammalian myeloid and lymphoid cell lines. Techniques for the propagation of mammalian cells in culture are well-known (see, Jakoby and Pastan (eds), 1979, Cell Culture, Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although other cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods *Methods in Enzymology* 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding a SPANX-B polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Methods of Treatment

In exemplary applications, a therapeutically effective amount of compositions are administered to a patient suffering from a disease, such as melanoma or lung, colon, renal, ovarian or breast carcinomas, in an amount sufficient to raise an immune response to SPANX-B-expressing cells. The methods can include selecting a subject in need of treatment, such as a subject with a tumor that expresses SPANX-B. SPANX-B is expressed in melanoma, hematological malignancies and myeloma, amongst other tumors (see, for example, Wang et al., *Blood* 101(3):955-60, 2003; Westbrook et al., *Clin Cancer Res* 10(1 Pt 1):101-12, 2004). SPANX-positivity may also indicate the presence of more aggressive skin tumors, particularly in distant, nonlymphatic metastatic melanomas (Westbrook et al., *Clin Cancer Res* 10(1 Pt 1):101-12, 2004). In addition, sera of cancer patients contained high titers of SPANX antibody (Westbrook et al., op. cit.). In several examples, the methods include selecting a subject with a cancer, such as a melanoma or a lung, colon, renal, ovarian or breast cancer. In one example, the subject has malignant melanoma.

Administration induces a sufficient immune response to slow the proliferation of such cells or to inhibit their growth, or to reduce a sign or a symptom of the melanoma or lung, colon, renal, ovarian or breast carcinoma. Amounts effective for this use will depend upon the severity of the disease, the general state of the patient's health, and the robustness of the patient's immune system. A therapeutically effective amount of the compound is that which provides either subjective relief of a symptom(s) or an objectively identifiable improvement as noted by the clinician or other qualified observer.

An immunogenic SPANX-B polypeptide can be administered by any means known to one of skill in the art (see Banga, "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated. In one embodiment, administration is by subcutaneous or intramuscular injection. To extend the time during which the SPANX-B polypeptide is available to stimulate a response, the peptide or protein can be provided as an implant, an oily injection, or as a particulate system. The particulate system can be a microparticle, a microcapsule, a microsphere, a nanocapsule, or similar particle (see, e.g., Banga, supra). A particulate carrier based on a synthetic polymer has been shown to act as an adjuvant to enhance the immune response, in addition to providing a controlled release. Aluminum salts can also be used as adjuvants to produce an immune response. The immunogenic SPANX-B polypeptide can be administered in a fusion protein with a chemokine (e.g., as described in U.S. Pat. No. 6,562,347, herein incorporated by reference) a defensin (e.g., as described in U.S. Pat. Publication No. 2005/0095257, herein incorporated by reference), or Hsp70.

In one specific, non-limiting example, an immunogenic SPANX-B polypeptide is administered in a manner to direct the immune response to a cellular response (that is, a cytotoxic T lymphocyte (CTL) response), rather than a humoral (antibody) response. A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinylseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

In yet another embodiment, to induce a CTL response to an immunogenic SPANX-B polypeptide, a MHC Class II-restricted T-helper epitope is added to the immunogenic SPANX-B polypeptide to induce T-helper cells to secrete cytokines in the microenvironment to activate CTL precursor cells. Thus, the method can include administering more than one immunogenic SPANX-B polypeptide, such as one or more polypeptides that induce CTLs and one or more polypeptide that induces helper T cells. The technique can further involve adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Immunotherapeutics to Treat Infectious Diseases and Cancer," in Powell et al., eds., *Vaccine Design, the Subunit and Adjuvant Approach*, Plenum Press, New York, 1995).

A pharmaceutical composition including an immunogenic SPANX-B polypeptide is thus provided. In one embodiment, the immunogenic SPANX-B polypeptide, or fragment thereof, is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770; all of which are incorporated by reference. A stabilizing detergent is any detergent that allows the components of the emulsion to remain as a stable emulsion. Such detergents include polysorbate 80 (TWEEN™) (Sorbitan-mono-9-octadecenoate-poly(oxy-1,2-ethanediyl); manufactured by ICI Americas, Wilmington, Del.), TWEEN™ 40, TWEEN™ 20, TWEEN™ 60, ZWITTERGENT™ 3-12, TEEPOL HB7™, and SPAN™ 85. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications (e.g., Schmolka, *J. Am. Oil. Chem. Soc.* 54:110, 1977, and Hunter et al., *J. Immunol* 129:1244, 1981) such as PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, e.g., to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

An adjuvant can be included in the composition. In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif.

Optionally, the subject an be administered a therapeutically effective amount of one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, *J. Surg. Oncol.* 68(2):122-38; Lotze et al., 2000, *Cancer J Sci. Am.* 6(Suppl 1):561-6; Cao et al., 1998, *Stem Cells* 16(Suppl 1):251-60; Kuiper et al., 2000, *Adv. Exp. Med. Biol.* 465:381-90). These molecules can be administered systemically to the host. It should be noted that these molecules can be co-administered via insertion of a nucleic acid encoding the molecules into a vector, for example, a recombinant pox vector (see, for example, U.S. Pat. No. 6,045,802). In various embodiments, the nucleic acid encoding the biological adjuvant can be cloned into same vector as the SPANX-B polypeptide coding sequence, or the nucleic acid can be cloned into one or more separate vectors for co-administration. In addition, nonspecific immuno-modulating factors such as *Bacillus* Calmette-Guerin (BCG) and levamisole can be co-administered.

In another embodiment, a pharmaceutical composition includes a nucleic acid encoding an immunogenic SPANX-B polypeptide or immunogenic fragment thereof. A therapeutically effective amount of the immunogenic SPANX-B polynucleotide can be administered to a subject in order to generate an immune response. In one specific, non-limiting example, a therapeutically effective amount of the immunogenic SPANX-B polynucleotide is administered to a subject to treat melanoma or lung, colon, renal, ovarian or breast carcinoma.

One approach to administration of nucleic acids is direct immunization with plasmid DNA, such as with a mammalian expression plasmid. As described above, the nucleotide sequence encoding an immunogenic SPANX-B polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In another approach to using nucleic acids for immunization, an immunogenic SPANX-B polypeptide can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In the embodiment where a combination of a first recombinant viral vector carrying a nucleic acid sequence of one or more SPANX-B polypeptides and a second recombinant viral vector carrying the nucleic acid sequence of one or more immunostimulatory molecules is used, the mammal can be immunized with different ratios of the first and second recombinant viral vector. In one embodiment the ratio of the first vector to the second vector is about 1:1, or about 1:3, or about 1:5. Optimal ratios of the first vector to the second vector may easily be titered using the methods known in the art (see, for example, U.S. Pat. No. 6,893,869, incorporated herein by reference).

In one embodiment the recombinant viruses have been constructed to express cytokines (such as TNF-α, IL-6, GM-CSF, and IL-2), and co-stimulatory and accessory molecules (B7-1, B7-2) alone and in a variety of combinations. Simultaneous production of an immunostimulatory molecule and the SPANX-B polypeptide enhances the generation of specific effectors. Without being bound by theory, dependent upon the specific immunostimulatory molecules, different mechanisms might be responsible for the enhanced immunogenicity: augmentation of help signal (IL-2), recruitment of professional APC (GM-CSF), increase in CTL frequency (IL-2), effect on antigen processing pathway and MHC expression (IFNγ and TNFα) and the like. For example, IL-2, IL-6, interferon, tumor necrosis factor, or a nucleic acid encoding these molecules, can be administered in conjunction with a SPANX-B immunogenic polypeptide, or a nucleic acid encoding a SPANX-B polypeptide. The co-expression of a SPANX-B polypeptide together with at least one immunostimulatory molecule can be effective in an animal model to show anti-tumor effects.

In one embodiment, a nucleic acid encoding an immunogenic SPANX-B polypeptide is introduced directly into cells. For example, the nucleic acid can be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 μg/kg to about 50 mg/kg, and typically are about 0.005 mg/kg to about 5 mg/kg (see, e.g., U.S. Pat. No. 5,589,466).

In one specific, non-limiting example, a pharmaceutical composition for intravenous administration would include about 0.1 μg to 10 mg of immunogenic SPANX-B polypeptide per patient per day. Dosages from 0.1 mg up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pa., 1995.

In another method, antigen presenting cells (APCs), such as dendritic cells (DCs), are pulsed or co-incubated with peptides comprising a SPANX-B polypeptide in vitro. In one specific, non-limiting example, the antigen presenting cells can be autologous cells. A therapeutically effective amount of the antigen presenting cells can then be administered to a subject.

In one embodiment, the SPANX-B polypeptides are used to produce artificial antigen presenting cells (aAPC). Artificial antigen presenting cells can be prepared by coupling HLA-A2 IG and anti-CD28 monoclonal antibody onto a solid support, such as DYNABEADS™ M-450 epoxy (Dyanl Biotech Inc., Lake Success, N.Y.) according to established procedures (see Oelke et al., *Nature Medicine* 9: 619-624, 2003; Durai et al., *Cancer Immunol. Immunother.* 58: 209-220, 2009, both herein incorporated by reference). As an example, for peptide loading, aAPC can be incubated with a peptide concentration of about 30 μg/ml at 4° C. for about 24 hours.

The SPANX-B polypeptide can be delivered to the antigen presenting cells, such as, aAPCs, dendritic cells, or dendritic cell precursors via any method known in the art, including, but not limited to, pulsing aAPCs or dendritic cells directly with antigen, or utilizing a broad variety of antigen delivery vehicles, such as, for example, liposomes, or other vectors known to deliver antigen to cells. In one specific, non-limiting example an antigenic formulation includes about 0.1 μg to about 1,000 μg, or about 1 μg to about 100 μg of a selected SPANX-B polypeptide. The SPANX-B polypeptide can also be administered with agents that promote dendritic cell maturation. Specific, non-limiting examples of agents of use are interleukin-4 (IL-4) and granulocyte/macrophage colony stimulating factor (GM-CSF), or flt-3 ligand (flt-3L). The preparation can also contain buffers, excipients, and preservatives, amongst other ingredients.

In one embodiment, mature antigen presenting cells are generated to present the immunogenic SPANX-B polypeptide. These antigen presenting cells, such as, but not limited to aAPC or dendritic cells, are then administered alone (or in combination with another agent) to a subject with a tumor that expresses SPANX-B, such as melanoma or lung, colon, renal, ovarian or breast carcinoma. In another embodiment, the aAPC or dendritic cells are administered in conjunction with a chemotherapeutic agent. These aAPCs or dendritic cells can be autologous.

Alternatively, the APCs (or aAPCs) are used to sensitize CD8 cells, such as tumor infiltrating lymphocytes (TILs) from tumors or peripheral blood lymphocytes (PBLs). The TILs or PBLs can be from the same subject (autologous) that is to be treated. Alternatively, the TILs or PBLs can be heterologous. However, they should at least be MHC Class-I restricted to the HLA types the subject possesses. An effective amount of the sensitized cells is then administered to the subject. Similarly, APCs (or aAPCs) can be used to generate activated CD4 cells, and these cells can be administered to a subject. These CD4 or CD8 cells can be autologous.

Peripheral blood mononuclear cells (PBMCs) can be used as the responder cell source of CTL precursors or helper T cell precursors. The appropriate antigen-presenting cells are incubated with peptide, after which the peptide-loaded antigen-presenting cells are then incubated with the responder cell population under optimized culture conditions. In one embodiment, when CTLs are generated, positive CTL activation can be determined by assaying the culture for the presence of CTLs that kill radio-labeled target cells, both specific peptide-pulsed targets as well as target cells expressing endogenously processed forms of the antigen from which the peptide sequence was derived, such as SPANX-B (for example, SEQ ID NO: 18).

The cells can be administered to a subject to inhibit the growth of cells of SPANX-B expressing tumors. In these applications, a therapeutically effective amount of activated antigen presenting cells, or activated lymphocytes, and/or T helper cells, are administered to a subject suffering from a disease, in an amount sufficient to raise an immune response to SPANX-B-expressing cells. The resulting immune response is sufficient to slow the proliferation of such cells or to inhibit their growth, or to reduce a sign or a symptom of the tumor.

In a supplemental method, any of these immunotherapies is augmented by administering a cytokine, such as interleukin (IL)-2, IL-3, IL-6, IL-10, IL-12, IL-15, GM-CSF, or interferons.

The compositions can be administered for therapeutic treatments. In therapeutic applications, a therapeutically effective amount of the composition is administered to a subject suffering from a disease, such as melanoma or lung, colon, renal, ovarian or breast carcinoma. Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, Kreuter, ed., Marcel Dekker, Inc., New York, N.Y., pp. 219-342, 1994; Tice & Tabibi, *Treatise on Controlled Drug Delivery*, Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342; and 5,534,496).

In a supplemental method, any of these immunotherapies is augmented by administering a cytokine, such as IL-2, IL-3, IL-6, IL-10, IL-12, IL-15, GM-CSF, interferons. In a further method, any of these immunotherapies is augmented by administering an additional chemotherapeutic agent. In one example, this administration is sequential. Examples of such agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II, also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs include adriamycin, melphalan (Alkeran®) Ara-C (cytarabine), carmustine, busulfan, lomustine, carboplatinum, cisplatinum, cyclophosphamide (Cytoxan®), daunorubicin, dacarbazine, 5-fluorouracil, fludarabine, hydroxyurea, idarubicin, ifosfamide, methotrexate, mithramycin, mitomycin, mitoxantrone, nitrogen mustard, paclitaxel (or other taxanes, such as docetaxel), vinblastine, vincristine, VP-16, while newer drugs include gemcitabine (Gemzar®), trastuzumab (Herceptin®), irinotecan (CPT-11), leustatin, navelbine, rituximab (Rituxan®) imatinib (STI-571), Topotecan (Hycamtin®), capecitabine, ibritumomab (Zevalin®), and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (Imreg, New Orleans, La.), SK&F 106528, and TNF (tumor necrosis factor; Genentech).

Reagents for the Detection of Cells that Express CD8 (CD8$^+$) Cells that Specifically Bind SPANX-B Reagents are provided herein for the detection of CD8-expressing cells that specifically bind SPANX-B. These reagents are tetrameric MHC Class I/immunogenic SPANX-B polypeptide complexes. These tetrameric complexes include an immunogenic SPANX-B polypeptide Tetrameric MHC Class I/peptide complexes can be synthesized using methods well known in the art (Altmann et al., *Science* 274:94, 1996, which is herein incorporated by reference). In one specific non-limiting example, purified HLA heavy chain and β2-microglobulin (β2m) can be synthesized by means of a prokaryotic expression system. One specific, non-limiting example of an expression system of use is the pET system (R&D Systems, Minneapolis, Minn.). The heavy chain is modified by deletion of the transmembrane and cytosolic tail and COOH-terminal addition of a sequence containing the biotin protein ligase (Bir-A) enzymatic biotinylation site. Heavy chain, β2m, and peptide are then refolded. The refolded product can be isolated by any means known in the art, and then biotinylated by Bir-A. A tetramer is then produced by contacting the biotinylated product with streptavidin.

In one embodiment, the streptavidin is labeled. Suitable labels include, but are not limited to, enzymes, magnetic beads, colloidal magnetic beads, haptens, fluorochromes, metal compounds, radioactive compounds or drugs. The enzymes that can be conjugated to streptavidin include, but are not limited to, alkaline phosphatase, peroxidase, urease and β-galactosidase. The fluorochromes that can be conjugated to the streptavidin include, but are not limited to, fluorescein isothiocyanate, tetramethylrhodamine isothiocyanate, phycoerythrin, allophycocyanins and Texas Red. For additional fluorochromes that can be conjugated to streptavidin, see Haugland, *Molecular Probes: Handbook of Fluores-* cent *Probes and Research Chemicals* (1992-1994). The metal compounds that can be conjugated to the streptavidin include, but are not limited to, ferritin, colloidal gold, and particularly, colloidal superparamagnetic beads. The haptens that can be conjugated to the streptavidin include, but are not limited to, biotin, digoxigenin, oxazalone, and nitrophenol. The radioactive compounds that can be conjugated to streptavidin are known to the art, and include but are not limited to technetium 99m ($^{99}$Tc), $^{125}$I, and amino acids comprising any radionuclides, including, but not limited to, $^{14}$C, $^{3}$H and $^{35}$S. Generally, streptavidin labeled with a fluorochrome is utilized in the methods disclosed herein.

In one embodiment, suspension of cells including T cells that specifically recognize SPANX-B is produced, and the cells are reacted with the tetramer in suspension. In one embodiment, these reagents are used to label cells, which are then analyzed by fluorescence activated cell sorting (FACS). A machine for FACS employs a plurality of color channels, low angle and obtuse light-scattering detection channels, and impedance channels, among other more sophisticated levels of detection, to separate or sort cells. Any FACS technique can be employed as long as it is not detrimental to the detection of the desired cells. (For exemplary methods of FACS see U.S. Pat. No. 5,061,620.)

The disclosure is illustrated by the following non-limiting Examples.

EXAMPLES

Hominid SPANX family (a sperm protein associated with the nucleus on the chromosome X) consists of highly homologous proteins that share about 40-50% similarity with each other. SPANX is encoded by an ancestral SPANX-N and its descendant SPANX-A/D genes (Kouprina et al., *Proc Natl Acad Sci USA* 101(9):3077-82, 2004) that contain two exons separated by a 650 bp intron with an inserted retroviral LTR sequence (Zendman et al., *Gene* 309(2):125-33, 2003). SPANX-A/D has five members (SPANX-A1, -A2, -B, -C, and -D) classified on the basis of diagnostic amino acid substitutions. The SPANX-A1, -C, and -D genes encode 97 amino acid proteins; while the SPANX-B gene, which can have up to a dozen copies, expresses a 103 amino acid protein (Kouprina et al., *Genome Res* 15(11):1477-86, 2005). SPANX is not expressed in nongametogenic adult tissues and its biological function is not well understood. However, based on their unique expression and localization in subpopulations of spermatids and spermatozoa (Westbrook et al., *Mol Hum Reprod* 12(11):703-16, 2006), SPANX proteins were proposed to participate in mammalian spermatogenesis. SPANX-A and SPANX-B are localized in nuclear craters and cytoplasmic droplets of ejaculated spermatozoa, respectively (Westbrook et al., *Biol Reprod* 64(1):345-58, 2001).

SPANX is a typical cancer-testis (CT) antigen, since SPANX genes are also specifically expressed in variety of human tumors and in normal testis (see, for example, Zendman et al., *Cancer Res* 59(24):6223-9, 1999). To date, the initial observation that SPANX-C (originally designated CTp11) was expressed in human melanoma (Zendman et al., op. cit.) was expanded demonstrating that the other members (SPANX-A1, -A2, and -B) were also present in melanoma, bladder carcinomas and hematological malignancies and myeloma (see, for example, Wang et al., *Blood* 101(3):955-60, 2003; Westbrook et al., *Clin Cancer Res* 10(1 Pt 1):101-12, 2004). The SPANX-positivity may also indicate the presence of more aggressive skin tumors, particularly in distant, nonlymphatic metastatic melanomas (Westbrook et al., *Clin Cancer Res* 10(1 Pt 1):101-12, 2004). In addition, sera of cancer patients contained high titers of SPANX antibody presumably generated during necrosis of malignant cells (Westbrook et al., op. cit.).

It is demonstrated herein that SPANX-B is widely expressed in human malignancies, particularly in melanoma and lung, ovarian, and breast carcinomas. In melanoma specifically, its expression was associated with advanced and metastatic disease. Moreover, it is demonstrated that SPANX-B is also recognized by the human T cell immune arm. Human peripheral blood contains T cell precursors that recognize SPANX-B, which can be readily expanded to generate the SPANX-B-specific CD4$^+$ and cytolytic CD8$^+$ T cells. The recognition epitopes have also been mapped demonstrating that SPANX-B contains at least one immunodominant HLA-DR- and two HLA-A2-restricted epitopes. These data, taken together, show that SPANX-B is a potent and clinically relevant therapeutic antigen for cancer immunotherapy.

Example 1

Materials and Methods

Human Peripheral Blood Cell Isolation: Human peripheral blood samples (PBMCs) were collected from healthy donors in accordance with Human Subject Protocol #2003054 by the Health Apheresis Unit and the Clinical Core Laboratory of the National Institute on Aging (NIA). CD4$^+$ T cells were isolated from PBMCs by negative selection using a human CD4 subset column kit (R&D Systems, Minneapolis, Minn.) after Ficoll-Paque (GE Healthcare Bio-Sciences, Piscataway, N.J.) density gradient separation according to the manufacturers' instructions. CD8$^+$ T cells were isolated using CD8 beads (Invitrogen, in a ratio 1 µl beads per 1×10$^8$ T cells in PBS with 0.1% BSA and 2 mM EDTA). Beads were removed from cells using DETACHaBEAD™ CD4/CD8 reagent (Dynal Biotech/Invitrogen). Cell purity was determined by FACS which resulted in 94% CD4$^+$ T cells and 98% CD8$^+$ T cells. Cells were cultured in RPMI with 10% FBS and 5% human serum (clone medium). Monocyte/macrophage-enriched PBMCs by plastic adherence were used for isolation of DCs. Briefly, immature dendritic cells were generated by five day culturing adherent cells in cRPMI with 10% FBS and 5% human serum containing 20 ng/mL rhIL-4 and 30 ng/mL rhGM-CSF. DCs were matured with overnight treatment with 10 µg/mL LPS (Sigma).

Reagents and cells: Recombinant SPANX-B protein fused with maltose binding protein (MBP) was produced and purified from *E. coli* using the pMAL protein expression and purification system according to manufacturer's instructions (New England Biolabs, Beverly, Mass.). Peptide sequences used in this work: Pep-1 (SPANX-C$_{80\text{-}89}$), LQMEEEEFM (SEQ ID NO: 1); Pep-2 (SPANX-B$_{23\text{-}31}$), EANEANKTM (SEQ ID NO: 2); Pep-3 (SPANX-B$_{2\text{-}10}$), GQQSSVRRL (SEQ ID NO: 3); Pep-4 (SPANX-B$_{57\text{-}65}$), LVVRYRRNV (SEQ ID NO: 4); Pep-5 (SPANX-C$_{12\text{-}35}$), RSVPCESNEVNETMPETPTGDSDP (SEQ ID NO: 5); Pep-6 (SPANX-B$_{42\text{-}65}$), QPAPKKMKTSESSTILVVRYR-RNV (SEQ ID NO: 6); Pep-7 (SPANX-B$_{66\text{-}89}$), KRTSPEELVNDHARENRINPDQME (SEQ ID NO: 7); Pep-8 (SPANX-B$_{80\text{-}103}$), ENRINPDQMEEEEFIEITTER-PKK (SEQ ID NO: 8); Pep-9 (SPANX-B$_{12\text{-}23}$), RSVPCESNEANE (SEQ ID NO: 9); Pep-9-Mod (SPANX-B$_{12\text{-}23}$-scrambled), RSAPCASAEVNE (SEQ ID NO: 13); Pep-10 (SPANX-C$_{8\text{-}16}$), GGVKRSVPC(SEQ ID NO: 10); Pep-11 (SPANX-C$_{86\text{-}94}$), EFMEIMVEI (SEQ ID NO: 11); Pep-12 (SPANX-BC$_{43\text{-}51}$, KTSESSTIL (SEQ ID NO: 12);

Pep-G1 (SPANX-B$_{11-31}$), KRSVPCESNEANEA-NEANKTM (SEQ ID NO: 14); Pep-G2 (SPANX-B$_{21-41}$), ANEANEANKTMPETPTGDSDP (SEQ ID NO: 15); MOPC (MOPC Igλ$_{91-101}$), ALWFRNHFVFGGGTK (SEQ ID NO: 16); and influenza HLA-A2 peptide M (Flu M1$_{58-61}$), GILGFVFTL (SEQ ID NO: 17). All peptides were custom designed and purchased from AnaSpec (San Jose, Calif.). The SPANX-B peptide-specific antibody ANEA-I0117 was generated by immunizing rabbits with SPANX-B-specific synthetic peptides. Antibodies specific to human IFNγ and to HLA-A,B,C were purchased from BD pharmingen (San Jose, Calif.); antibodies to HLA-DR, HLA-DP and HLA-DQ were from Leinco (St. Louis, Mo.).

The majority of cell lines, such as 938 Mel, Jurkat, CCRF-CEM (CEM, CCL-119), and CRL 7002, were purchased from ATCC (Manassas, Va.), with the exception of the UACC1273 and OVCAR3 cell line. The cells were grown in cRPMI supplemented with 10% FBS. Human embryonic kidney cells (HEK293, ATCC) were grown in cDMEM with 10% FBS; ovarian cancer cell lines 2008, BG-1, and OVCAR3 were grown in cMcCoy's 5A medium supplemented with 10% FBS. Human primary melanoma cells Tc526, Tc624, Tc2492, Tc2547 and Tc938 were cultured in cRPMI supplemented with 10% FBS. All cells were maintained in a 37° C. humidified 5% $CO_2$. Collection of paraffin non small cell lung cancer (NSCLC) blocks was obtained from seven different patients.

T cell stimulation: To generate CD4$^+$ T cell lines, CD4$^+$ T cells (2×10$^6$) were stimulated with autologous DC pulsed with either SPANX-B protein (2 μg/mL), or with SPANX-B peptides (10 μg/mL) in the presence of IL-2 (20 U/mL) for seven days. T cells were re-stimulated once every week two times. To generate CD8$^+$ CTL lines, 2×10$^6$ CD8$^+$ T cells were stimulated with autologous DC pulsed with either SPANX-B protein (2 μg/mL) and SPANX-B peptides (10 μg/mL) in the presence of IL-2 (20 U/mL) and IL-15 (10 ng/mL) for seven days. T cells were weekly restimulated with peptide-loaded DCs for several times. To test antigen-specific activity of CD4$^+$ T cell lines, all experiments were performed in triplicates in 96-well plates with 1×10$^5$ CD4$^+$ T cells/well. The cells were stimulated with autologous DCs incubated overnight with SPANX-B protein, or SPANX-B or control peptides (0.1 and 0.01 μg/mL) in clone medium with (20 U/mL). T cell activity was judged by IFNγ secretion in culture supernatants by ELISA after 48 hours incubation (see below and Schiavo et al., *Blood* 107(12):4597-605, 2006). For most experiments, unless specified, 1:5 Target:Effector ratio was used.

Detection of IFNγ by ELISA: ELISA was performed as described elsewhere (Schiavo et al., *Blood* 107(12):4597-605, 2006). Briefly, 96-well flat-bottom plates were coated with 2 μg/mL of anti-human IFNγ antibody (BD pharmingen, San Jose, Calif.) to capture secreted IFNγ. The captured IFNγ was detected with 0.5 μg/mL biotin-conjugated mouse anti-human IFNγ antibody and streptavidin-HRP (BD pharmingen, San Jose, Calif.). The assay was visualized with TMB peroxidase solution B (KPL, Gaithersburg, Md.) and read at $OD_{450}$.

CTL assay and HLA blocking experiments: Tumor cell lines (target cells, 2×10$^6$) were incubated in 200 μL of fetal bovine serum (FBS) with 200 μCi of Na$_2^{51}$CrO$_4$ (PerkinElmer, Billerica, Mass.) for 2 hours at 37° C. Cells were washed with RPMI three times and resuspended in cRPMI with 10% FBS at 1×10$^5$ cells/mL. CTL assay was performed in triplicate in 96-well round bottom plates with 1×10$^4$/well $^{51}$Cr-labeled target cells. The target cells were co-cultured at indicated ratios with effector cells (peptide-specific CD8$^+$ T cells) for 6 hours. The specific $^{51}$Cr-release is calculated using formula: ((test sample release−spontaneous release)/(maximum release−spontaneous release))×100). Maximum release is for the target cells alone lysed with 2% Triton X-100.

The MHC class I and class I inhibition assays: HLA specific mAbs or control isotype matched IgG were preincubated with peptide-pulsed DCs at concentration of 10 μg/mL for one hour at 4° C. Cells were washed with PBS, irradiated at 4500 rad and mixed with T cells at indicated ratios. To block HLA class I expression, tumor cells lines were pretreated with 10 μg/mL of anti-HLA-A,B,C antibodies (BD Pharmingen, San Jose, Calif.) for one hour at 4° C. Cells were washed with PBS and labeled with $^{51}$Cr as indicated above. IFNγ production was determined by ELISA after 48 hour incubation as described (Schiavo et al., *Blood* 107(12):4597-605, 2006).

Detection of SPANX-B expression in human tumors: SPANX-B mRNA expression was tested and confirmed using RT-PCR utilizing combinations of two different sets of primers that amplify spliced messages, such as forward and reverse primers designed in house (PRSPANXB-Lar-1: 5'-ATGGGCCAACAATCCAGTGT-3' (SEQ ID NO: 20), and PRSPANXB-Lar-R1: 5'-CTTTTTAG-GTCTTTCAGTCGT-3' (SEQ ID NO: 21), respectively); and forward and reverse SPANX-B primers reported by others (5'-ACTGTAGACATCGAAGAACC-3' (SEQ ID NO: 22), and 5'-TTGATTCTGTTCTCTCGGGC-3' (SEQ ID NO: 23); Lilljebjorn et al., *Leukemia* 21:2137-2144, 2007).

Total RNA, extracted from frozen cell pellets using RNeasy Mini Kit (Qiagen, MD), was reverse transcribed using M-MLV RT (Invitrogen) and amplified using 2 U Taq DNA polymerase (New England Biolabs Inc., Beverly, Mass.): 35 cycles of 94° C. for 1 min, 60° C. for 1 min, and 72° C. for 1 min. Control amplification was for expression of GAPDH using PRuGAPDH-1 and PRuGAPDH-R1 primers (5'-TGTGGAAGGGCTCATGACCACAGTCCAT-3' (SEQ ID NO: 24), and 5'-GCCTGCTTCACCACCTTCTTGATG-3' (SEQ ID NO: 25), respectively).

SPANX-B protein expression was detected using ANEA-I0117 anti-SPANX-B Ab (1:5000) in Western blotting of tumor lysates with 30 μg total protein separated in reducing 14% PAAG gels (Invitrogen, Carlsbad, Calif.). Bands were detected with ECL plus Western blotting detection system (GE healthcare, Little Chalfont Buckinghamshire, UK).

Immunohistochemistry staining for SPANX-B was performed on Multi-Tumor Tissue Arrays (T-MTA-5, Tissue Array Research Program, NCI, available on the internet) or on paraffin embedded biopsies of human with melanoma and NSCLC lung cancer. Briefly, the tissue slides were treated with series of xylene (three times for 5 min), ethanol 100% (two times for 2 min), ethanol 90%, ethanol 80%, ethanol 75% (one time for 2 min), PBS and water. Antigen retrieval was performed with citrate buffer in a steamer for 25 min. Slides were rinsed with PBS and blocked for 5 min with V block solution (LabVision Corp, Fremont, Calif.) and one hour with blocking buffer (0.2% Triton X-100, 0.2% casein, 0.2% BSA, 5% normal goat serum, 0.2% gelatin and 0.02% NaN$_3$). To perform immunohistochemistry staining on cultured cells, 3×10$^4$ tumor cell lines were seeded in an 8-well chamber slide (Lab-Tek II Chamber slide system). Cells were washed twice with PBS and fixed with 300 μL of Methanol: H$_2$O$_2$ 3% for 30 min. After several PBS washes, the cells were blocked with ultra V block solution (Lab Vision), rinsed with PBS and blocked with 200 μL of blocking buffer for one hour. The slides were treated with ANEA-I0117 anti-SPANX-B Ab (1:500) or control rabbit Ig for 2 hours at room temperature. Slides were washed three times in PBS, incubated for 30 min with biotinylated goat anti-rabbit antibody (Lab Vision), washed three times with PBS and incubated with streptavidin-peroxidase (Lab Vision) for 20 min. Protein expression was visualized with DAB (Lab Vision); and counterstained with hematoxylin.

Data analysis of the Mannheim data set: Scaled gene expression data were generated from the Affymetrix HG-U133 microarray chips for 45 primary cultures of melanoma biopsies using accession number GSE4843 (Mannheim data set, available on the internet at the NCBI website). This data was loaded into GeneSpring GX 7.3 (Agilent Technologies, Palo Alto, Calif., USA) and normalized as previously described (Hoek et al., Pigment Cell Res 19(4):290-302, 2006). Normalized data for the Motif 2 set of genes (averaged within each sample expression pattern (Hoek et al., op. cit.)) was compared to the expression pattern for SPANX-$B_1$ (probe set 220921_at) and the correlation coefficient was calculated; and statistical significance of variation of SPANX-B between the cohorts was calculated using Student's two-tailed t-test.

Example 2

SPANX-B Protein is Uniquely Expressed in Human Tumors

SPANX-B can be often found in the list of highly expressed genes in microarray study of human tumors, including hematological malignancies and breast cancer (see, for example, Minn et al., Nature 436(7050):518-24, 2005). To confirm this, expression was tested using two antibodies, a rabbit 3ANEA Ab and mouse SPANX-B Ab. The 3ANEA Ab was reported to be specific for the amino-terminal portion of SPANX-B in human spermatozoa (Kouprina et al., PLoS One 2:e359, 2007), and it specifically detected an expected size (about 15 Kd) band in SPANX-B-transduced murine RL5 cells in western blotting (FIG. 1A). The second SPANX-B Ab was produced from mice DNA immunized with SPANX-B-expressing plasmid. It was also specific for SPANX-B, as it preferentially recognized Pep-G1 peptide (FIG. 1B) encoding the amino-terminus of SPANX-B (FIG. 1C), but not other region-specific peptides, such as Pep-G2, Pep-2, Pep-3 and Pep-6 (FIGS. 1B and C). In support, it failed to recognize Pep-5 peptide that encoded the overlapping Pep-G1, but homologous with SPANX-C, portion (FIGS. 1B and C). In contrast, it reacted with a second peptide Pep-2 that only represented unique for SPANX-B insert of Pep-G1 (FIGS. 1B and C).

Figure 1E:
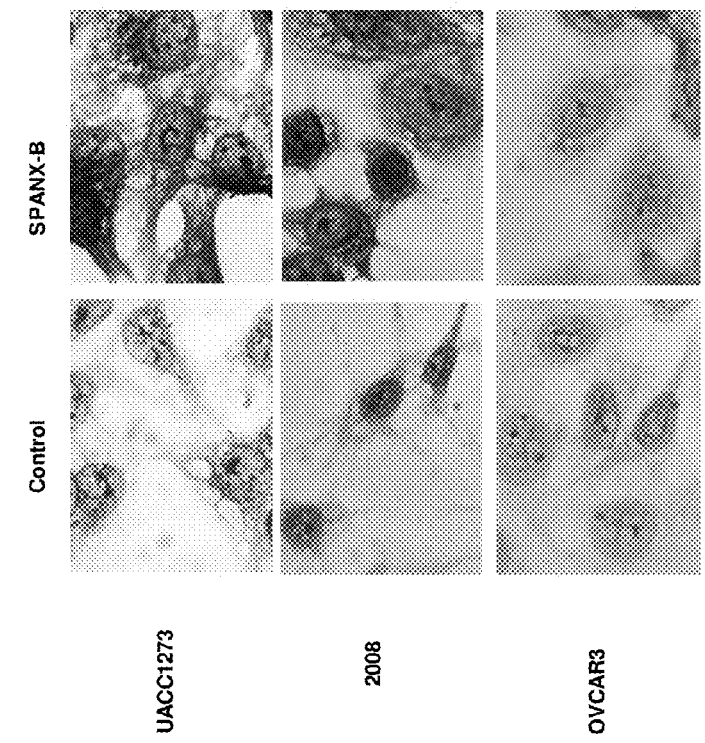
Figure 1F:
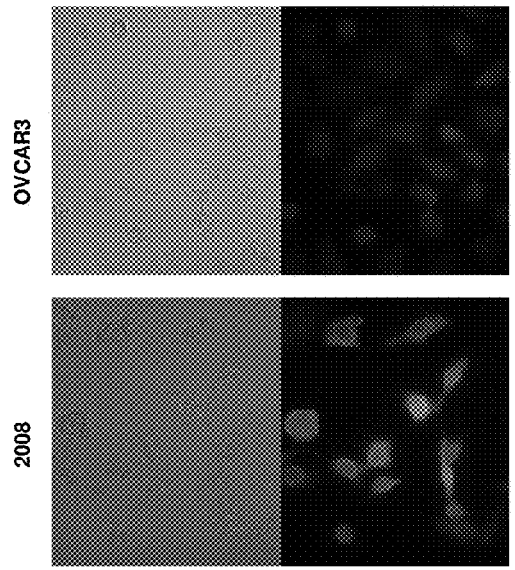
Figure 2A:
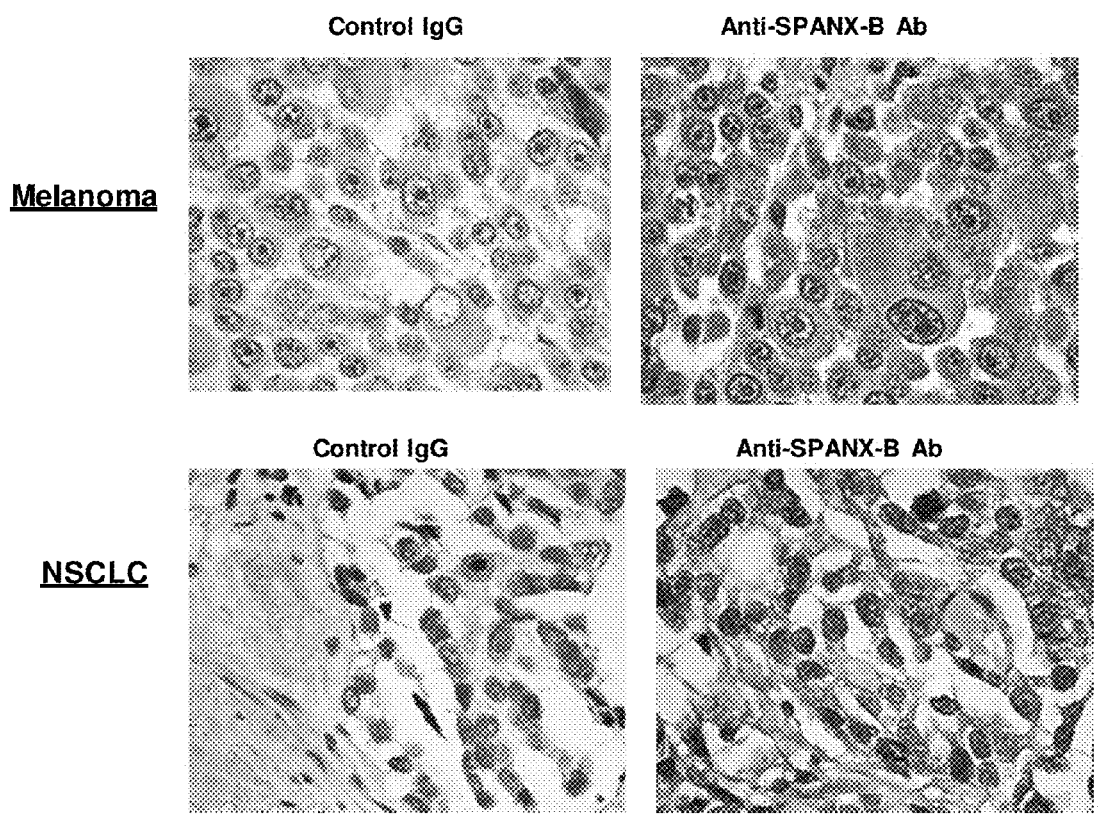
FIGS. 2A-2D are digital images and a graph showing SPANX-B is expressed in human primary tumors.
Figure 2B:
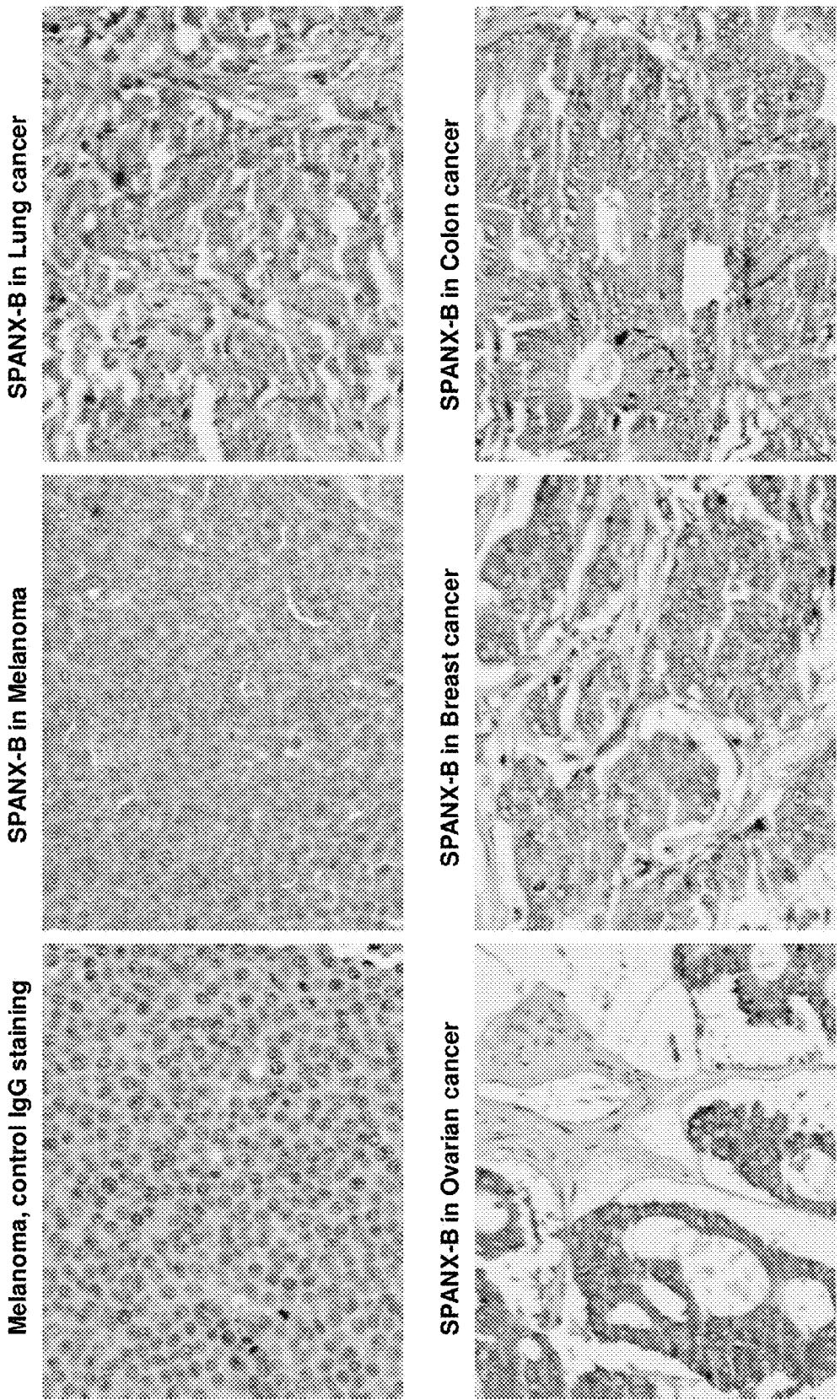
Figure 2C:
Figure 2D:
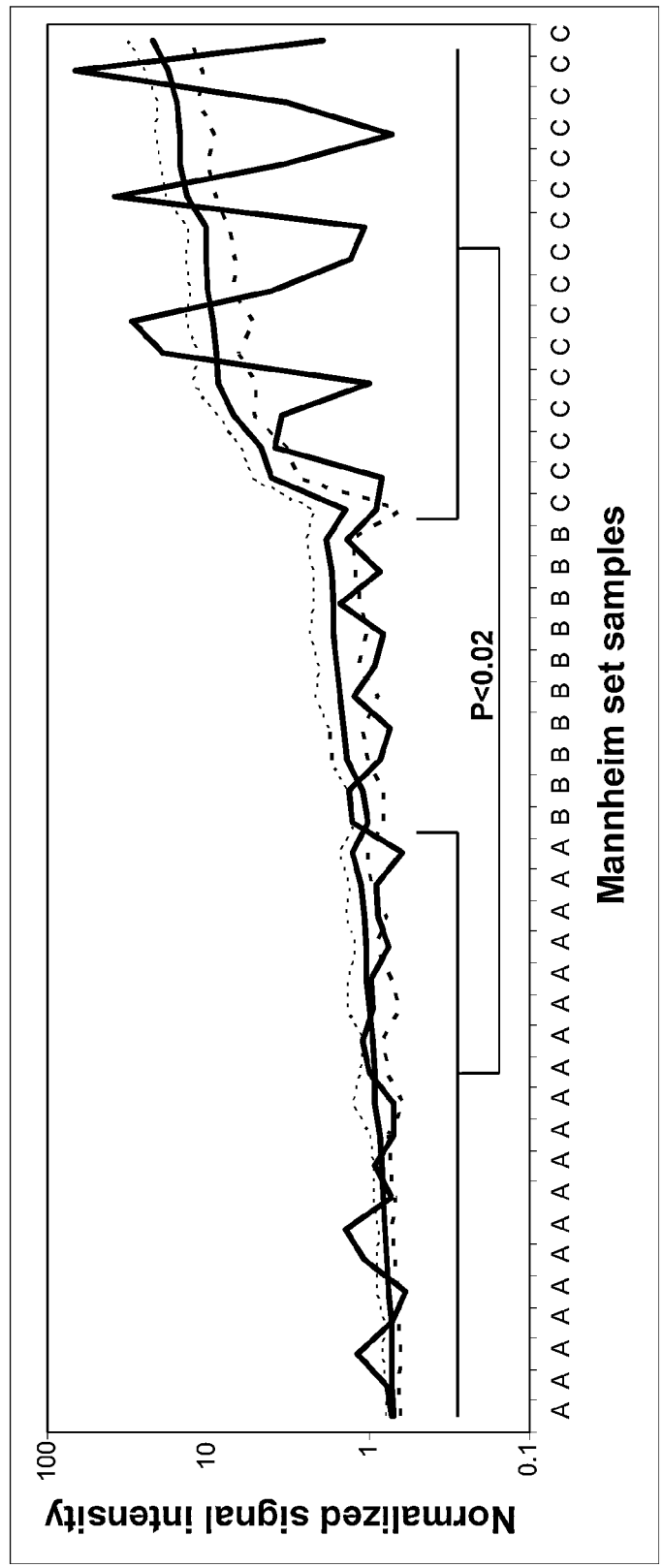

In concordance with RT-PCR data, SPANX-B was detected in lysates of immortalized human tumor lines, such as melanoma cells (UACC1273 and 938 Mel, FIG. 1D), and carcinomas of colon (HCC2998), and ovarian (IGROV 1), renal (786-0 and UO-31) and NSCLC (NCI H226). In contrast, SPANX-B was not detected in lysates of normal human PBMCs (FIG. 1D) and cell lines, such as HCT116 and HCT15 (colon cancer), OVCAR3 and OVCAR4 (ovarian cancer), and A498 and ACHN (renal cancer) and HOP62 and NCI H522 (NSCLC). These data were also supported by the immunohistochemistry staining of the cells. For example, SPANX-B-expressing cells, such as UACC1273 and 2008 cells (FIG. 1D), but not SPANX-B negative OVCAR3 cells, were also positive both in immunohistochemistry (FIG. 1E) and immunofluorescence (FIG. 1F) staining. The staining of primary human tumor samples revealed that it was expressed in human melanoma (2/2) and lung carcinoma (5/5, NSCLC) (FIG. 2A). Furthermore, the survey of a panel of human primary 145 tumors on a multitumor tissue microarray (T-TMA) has revealed that SPANX-B was expressed in ovarian, colon, breast and lung cancers, besides melanoma (see a representative picture in FIG. 2B). Although we did not intend to study normal human tissues, SPANX-B was detected in the limited numbers of normal tissues included in T-TMA, such as normal endometrium and colon (FIG. 2C). However, it was abundantly expressed in Sertoli cells of normal testis (FIG. 2C), indicating that SPANX-B is a typical cancer/testis-associated (CT) antigen. The expression of SPANX-B was variable, ranging from an abundant production in melanoma and ovarian carcinomas, to low or almost undetectable levels in T cell tumors (Jurkat and CEM, respectively, FIG. 1D). At least in melanoma, the presence of SPANX-B may indicate a metastatic stage of the disease, as its expression was associated with a group of genes expressed in melanoma with the highest metastatic potential (Cohort C in Mannheim data set (Hoek et al., Pigment Cell Res 2006 August; 19(4):290-302), correlation co-efficient 0.503; FIG. 2D). In contrast, no association was found in Cohort A that consisted of highly proliferative cells with low metastatic potential.

Example 3

Characterization of SPANX-B-Specific $CD4^+$ T Cell Responses

Figure 3A:
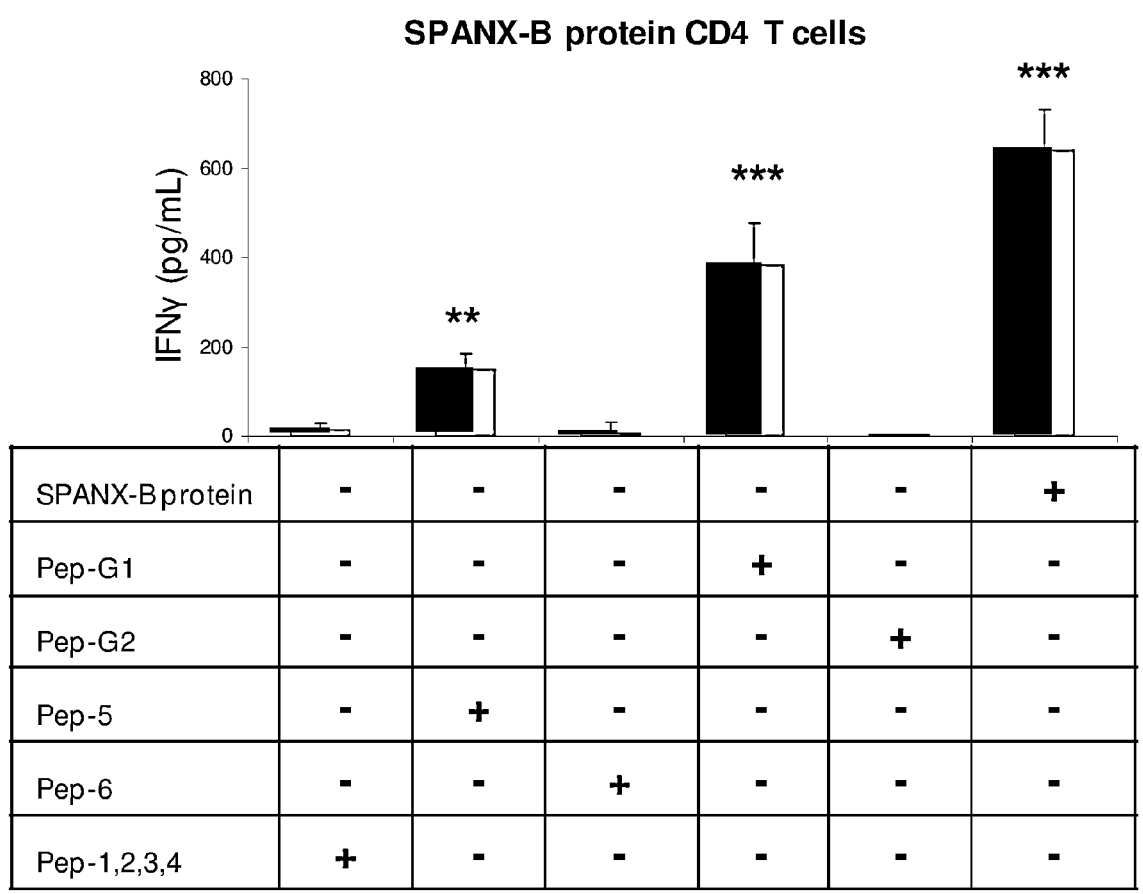
Figure 3B:
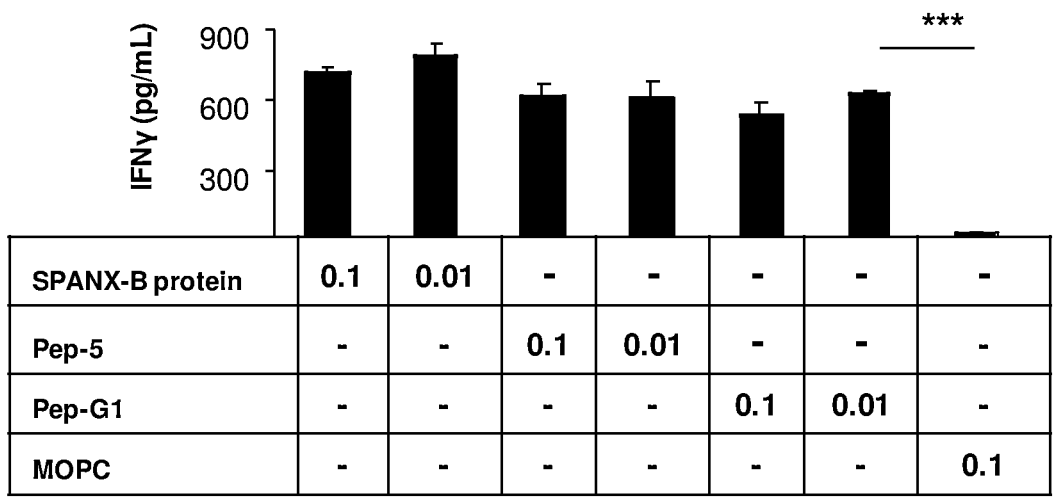
Figure 3C:
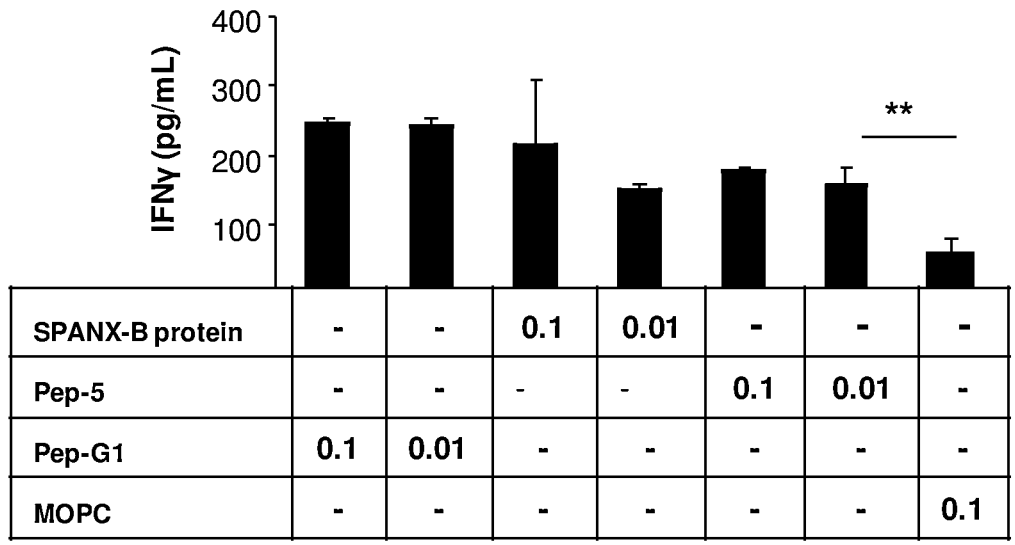

The clinical and therapeutic relevance of tumor associated antigens (TAA) depends on its ability to induce and expand the antigen-specific T cell precursors. To test this, human peripheral blood $CD4^+$ T cells were stimulated with autologous DCs incubated with SPANX-B protein. As a result, this allowed generation of SPANX-B-specific $CD4^+$ T cell lines from almost every human donor; the cells specifically recognized SPANX-B-treated DCs, but not control antigen-treated DCs, by secreting IFNγ (SPANX-B protein, FIG. 3A). To determine an immunodominant epitope, the $CD4^+$ T cells were stimulated with DCs pulsed with synthetic peptides to various parts of SPANX-B (FIG. 1C). Among them, two peptides from the amino-terminal portion of SPANX-B, $SPANX_{11-31}$ or $SPANX_{12-35}$ (Pep-G1 and Pep-5, FIG. 1C), activated the $CD4^+$ T cell lines to secrete IFNγ (FIGS. 3A and B). In contrast, the $CD4^+$ T cells failed to respond to DCs pulsed with other SPANX-B peptides, including peptides $SPANX_{21-41}$ (Pep-G2) and $SPANX_{42-65}$ (Pep-6), or mixture of Peptides 1-4 (Pep-1, 2, 3, 4, FIG. 3A), or control MOPC peptide (FIGS. 3B and C). Together, the MHC class II immunodominant region (epitope) is probably located within overlapping portion of Pep-G1 and Pep-5 between residues 11 and 35 of SPANX-B. The region was recognized by almost every normal human donor $CD4^+$ T cells tested (9/9), indicating that humans contain a pre-existing pool of precursor T cells specific for SPANX-B. In support, SPANX-B-specific $CD4^+$ T cell lines were also independently and readily generated using peptides Pep-5 and Pep-G1 (FIGS. 3C and D, respectively) that also specifically and in a dose-dependent manner recognized DCs incubated with SPANX-B protein.

Example 4

The Immunodominant Epitope of SPANX-B is Recognized in HLA-DR-Restricted Fashion To fine map the epitope, a shorter peptide Pep-9 (SPANX-$B_{12-23}$, FIG. 1C), which represents an overlapping portion of peptides Pep-5 and Pep-G1, was tested. Autologous DCs pulsed with Pep-9 were indeed able to activate the SPANX- B-specific CD4+ T cell lines (independently generated to SPANX-B protein, or Pep-1, or Pep-G1) to secrete IFNγ (a representative result on the Pep-G1-specific CD4+ T cells is shown in FIG. 3D). In contrast, the CD4+ T cells did not respond when stimulated with scrambled Pep-9 peptide (Pep-9-Mod, FIG. 3D). Together, the CD4+ T cells recognized an immunodominant epitope encoded "RSVPCESNEANE" (SEQ ID NO: 9) sequence of Pep-9 (FIG. 1C).

Figure 4A:
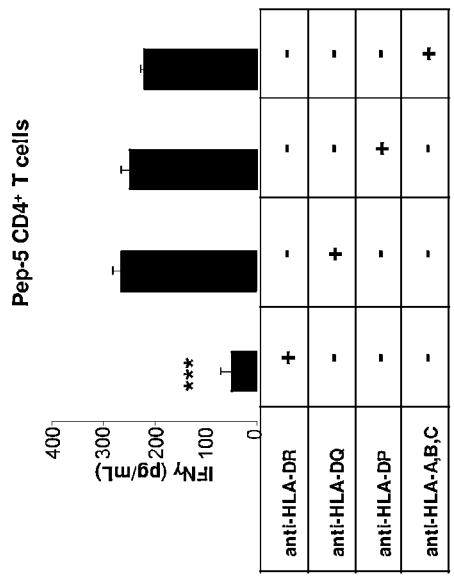
FIGS. 4A to 4C are bar graphs and tables showing the MHC Class II immunodominant epitope of SPANX-B is presented in the context of HLA-DR. The Pep-9-induced activation of the CD4+ T cell lines, generated to SPANX-B protein (FIG. 4A), or Pep-5 (FIG. 4B), or Pep-9 (FIG. 4C) can be abrogated by the presence of anti-HLA-DR Ab. In contrast, the presence of antibodies to HLA-DQ, or HLA-DP or MHC class I (anti-HLA-A,B,C) did not affect activity of CD4+ T cells. ***$P<0.001$ value is for comparison with the group indicated by line. The mean±SEM of representative and reproducible results of two independent experiments performed in triplicate for each panel are shown.
Figure 4B:
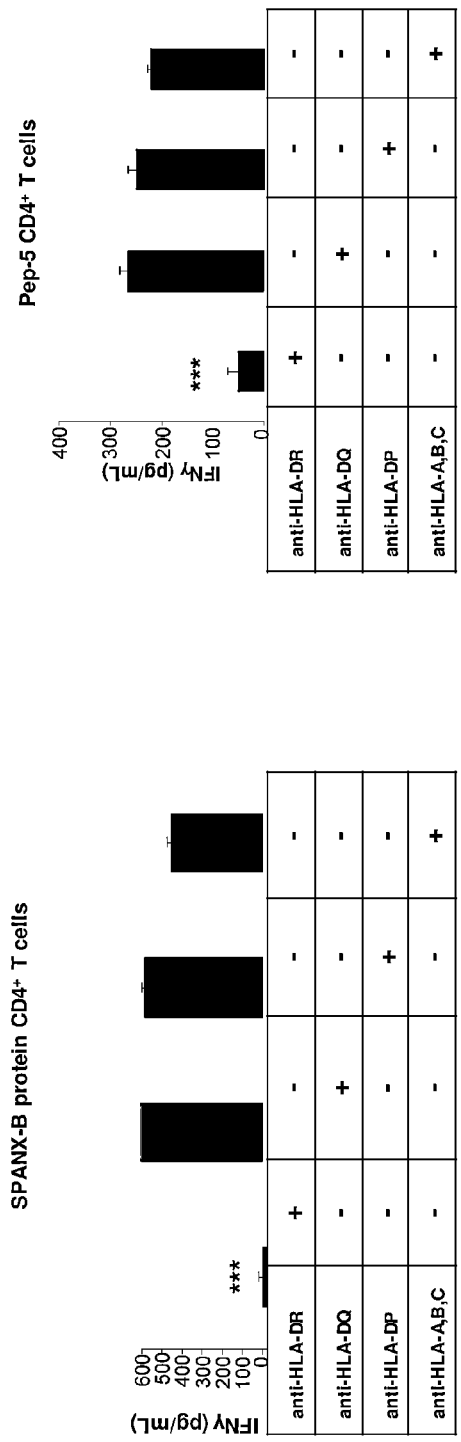
Figure 4C:
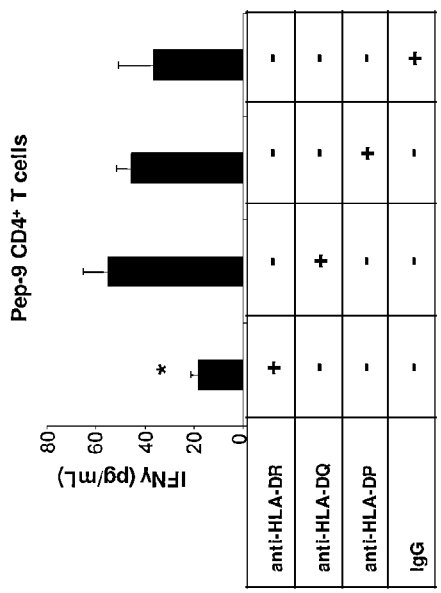

Next, to characterize HLA specificity, the CD4+ T cell lines were stimulated with autologous DCs pulsed with Pep-9 in the presence of antibody that blocked HLA-DR, or HLA-DQ, or HLA-DP molecules. The stimulation of the SPANX-B-specific CD4+ T cells was not affected by the presence of control antibody or antibodies that block HLA-DQ, or HLA-DP, or anti-MHC class I (FIGS. 4 A-C). In contrast, anti-HLA-DR Ab completely abrogated the Pep-9-induced IFNγ secretion from all CD4+ T cell lines specific to SPANX protein (FIG. 4A), or Pep-5 (FIG. 4B), or Pep-9 (FIG. 4C), respectively. Thus, the peptide Pep-9 represents an immunodominant epitope recognized by human CD4+ T cells in HLA-DR-restricted fashion.

Example 5

SPANX-B is Also Recognized by CD8+ T Cells in HLA-A2 Context

Figure 5A:
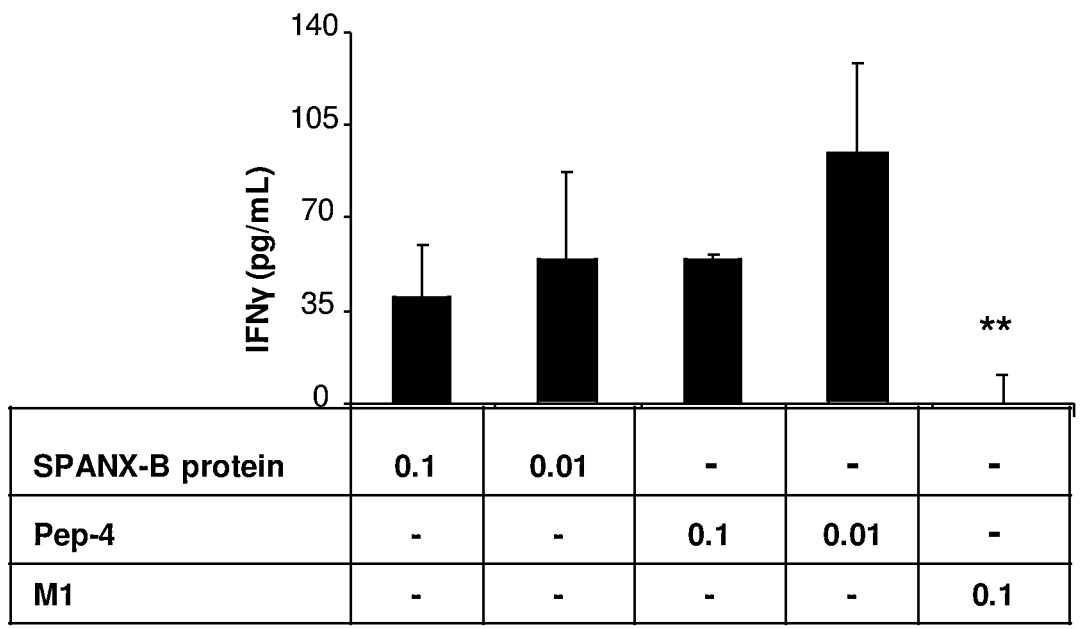
FIGS. 5A-5B are bar graphs and tables showing that SPANX-B polypeptides also induce CD8+ T cell responses. The SPANX-B-specific CD8+ T cell lines were generated by stimulating human CD8+ T cells with DCs fed with SPANX-B protein (FIG. 5A), or Pep-2 (FIG. 5B) or Pep-4. The CD8+ T cell lines specifically recognized and secreted IFNγ (pg/ml) upon stimulation with DCs incubated with titrated amounts (µg/ml) of SPANX-B protein, or Pep-4, but not control M1 Flu peptide (M1). The results presented in FIG. 5B illustrate that the CD8+ T cell recognition is MHC class I restricted, as the presence of anti-HLA I Ab, but not control isotype-matched Ab (IgG), abrogated IFNγ secretion from the SPANX-B-specific CD8+ T cells stimulated with mDCs pulsed with Pep-2. The same was observed for other CD8+ T cell lines generated by Pep-2- or Pep-4-pulsed DCs. *$P<0.05$ (FIG. 5A) and **$P<0.01$ (FIG. 5B) value is for comparison with IgG and M1 groups, respectively. The mean±SEM of representative and reproducible results of at least two independent experiments performed in triplicate for each panel are shown.
Figure 5B:
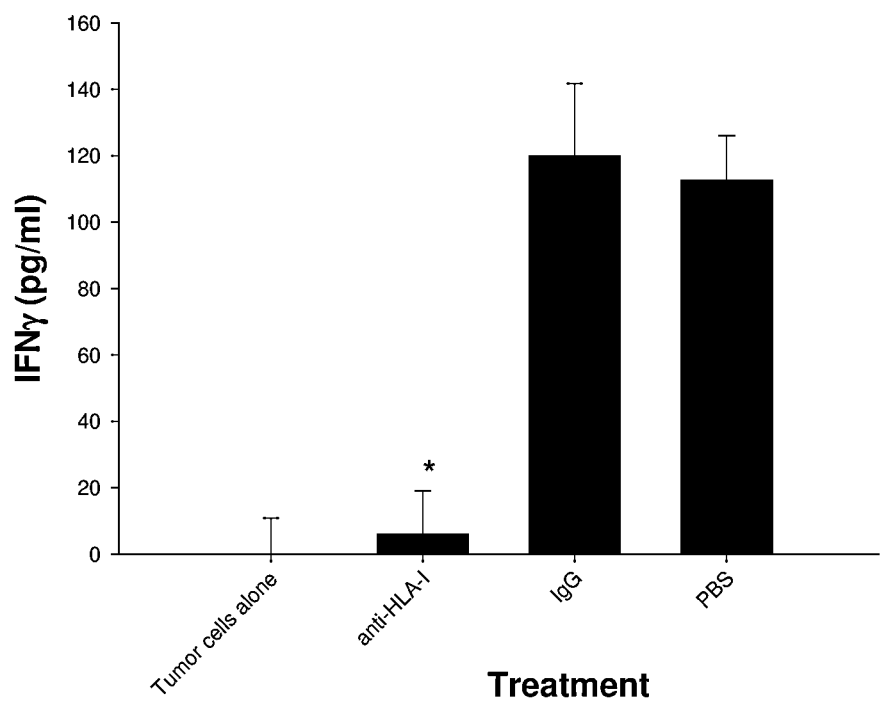

To exploit the full therapeutic value of TAAs, the induction of CD8+ T cells is required. Computer analysis of SPANX-B protein revealed two 9-mer peptides designated Pep-2 and Pep-4 (SPANX-B$_{23-31}$ and SPANX-B$_{57-65}$, respectively) that contained moderate Parker binding scores for HLA-A2 (see the bimas website, available on the internet). To test whether they are recognized by human CD8+ T cells, HLA-A2-positive peripheral blood CD8+ T cells were stimulated with autologuos DCs incubated with SPANX-B protein. As a result, SPANX-B-specific CD8+ T cell lines were generated from every donor PBL (3/3). The CD8+ T cells secreted IFNγ upon incubation with irradiated autologous DCs that were pulsed with SPANX-B protein or Pep-4 (FIG. 5A), or Pep-2. Reciprocally, the CD8+ T cells that were independently generated by Pep-2- or Pep-4-pulsed DCs also recognized SPANX-B protein-pretreated DCs. The recognition was specific, as no IFNγ was produced when the CD8+ T cells were stimulated with DCs pulsed with control HLA-A2-positive Matrix 1 influenza peptide (M1, FIG. 5A). Furthermore, this was the MHC class I restricted recognition, as SPANX-B-induced activation was specifically and significantly abrogated by the presence of anti-MHC-I, but not control, antibody (FIG. 5B).

Example 6

The SPANX-B-Specific CD8+ T Cells Kill Human Tumor in HLA-A2 Context

Figure 6A:
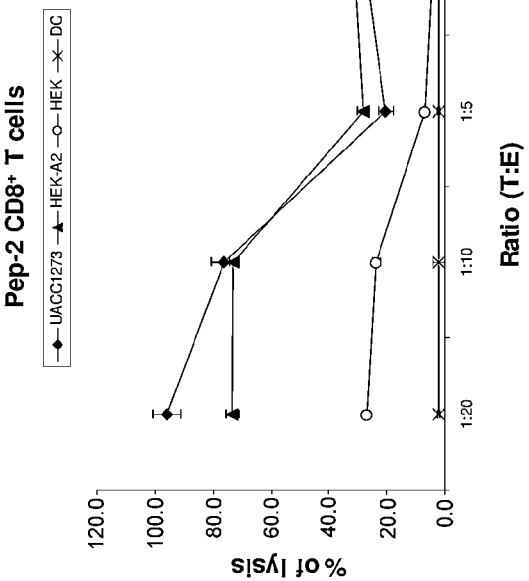
FIGS. 6A-6E are a set of graphs illustrating that the SPANX-B-specific CD8+ T cells recognize and kill HLA-A2-expressing melanoma cells. Effector CD8+ T cells (FIG. 6E) generated by stimulating with SPANX-B protein (FIG. 6A), or Pep-2 (FIG. 6B), or Pep-4 (FIG. 6C) were mixed with target (T) UACC1273 melanoma cells at the indicated ratio (X-axis) to perform cytolytic 6-hour $^{51}$Cr release assay. Control targets were parental (HEK) or HLA-A2-expressing (HEK-A2) HEK293 cells that were pulsed with 1 µg/ml Pep-2. Autologous DCs alone were used as a negative control group.
Figure 6B:
Figure 6D:
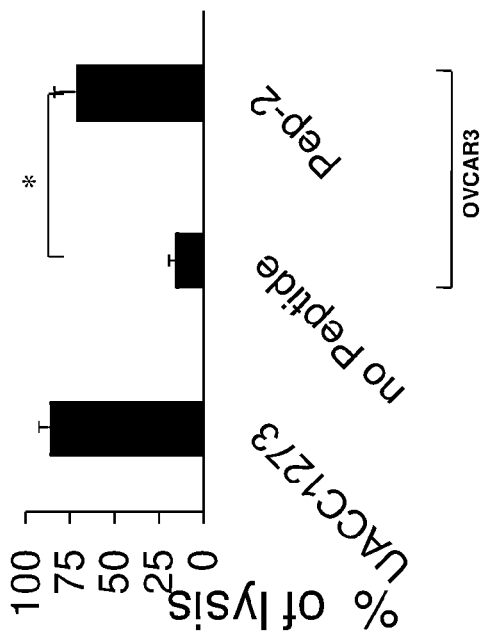
Figure 6C:
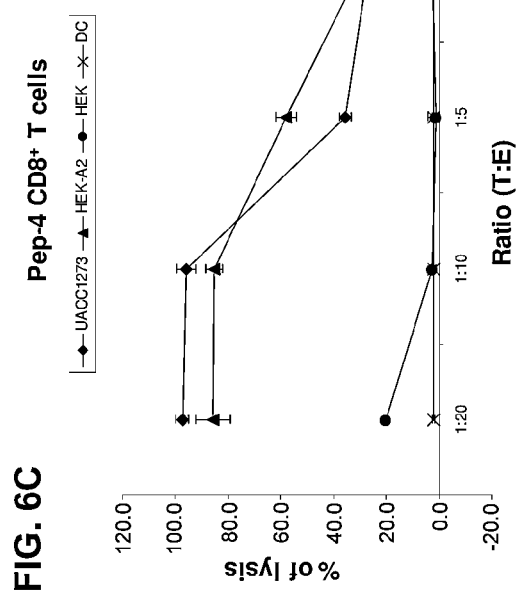
Figure 6E:
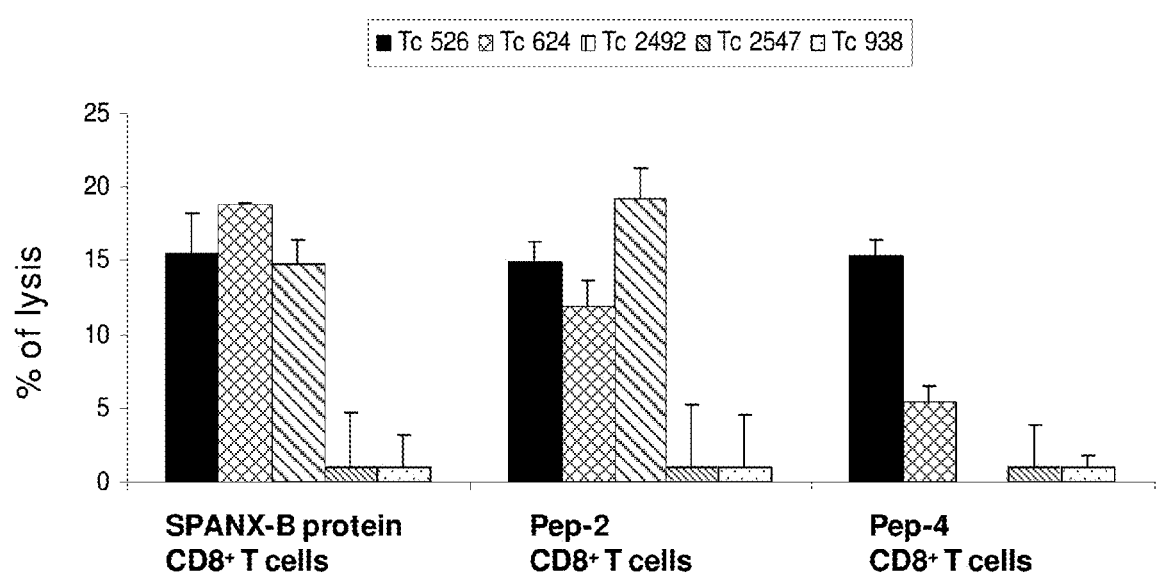

It was tested whether the CD8+ T cells can recognize human tumors that express SPANX-B. As shown in FIG. 6, the CD8+ T cells were able to kill melanoma cells. For example, they recognized and lysed SPANX-B-expressing and HLA-A2-positive UACC1273 melanoma cells (UACC1273, FIGS. 6A-C). Several lines of evidence indicate that is indeed HLA-A2-restricted response. First, the CD8+ T cells did not lyse HLA-A2-negative but SPANX-B-expressing melanoma cells 938 Mel. Second, all three types of CD8+ T cell lines (independently generated to SPANX-B protein, or Pep-2, or Pep-4) not only killed UACC1273 melanoma cells, but also lysed HLA-A2-expressing HEK293 cells that were pulsed with Pep-2 (HEK-A2, FIGS. 6A-C). In contrast, the CD8+ T cells did not kill HLA-A2-negative parental HEK293 cells (HEK, FIGS. 6A-C). Lastly, the CD8+ T cells could not lyse HLA-A2-positive OVCAR3 cells that did not express SPANX-B, unless pulsed with Pep-2 (FIG. 6D). Furthermore and importantly, all three CD8+ lines also recognized and lysed primary tumors from melanoma patients that expressed HLA-A2 (Tc526, Tc624 and Tc2492, FIG. 6D), while HLA-A2-negative tumors were not affected (Tc2547 and Tc938, FIG. 6E). Thus, humans contain a readily available proportion of circulating CD8+ T cells (at least precursors) that recognize two epitopes of SPANX-B, Pep-2 and Pep-4, presented on the MHC class I molecules in the HLA-A2 context.

The SPANX family proteins, specifically SPANX-C (CTp11), are usually produced in normal human sperm cells, but was found also expressed in melanoma and cancer cells of kidney, bladder and prostate. However, due to the lack of specific antibodies that discriminate each member of the family, no systemic study on the expression of SPANX-B in human tumors was reported. To date, its expression in melanoma, testicular germ cell tumors, and hematopoietic malignancies was detected mostly by the use of RT-PCR analysis (Zendman et al., supra). Here, the RT-PCR results were re-evaluated using two different SPANX-B specific antibodies that were specific to a unique 6 amino acid insert only present in SPANX-B. SPANX-B was found in a number of different tumors, besides melanoma. The SPANX-B-specific exon 1 fragment was also amplified by RT-PCR in all ten randomly chosen positive samples. Together, the antibodies used in this study are specific, although due to a high homology between SPANX-A/D members the issue of cross-reactivity may not be fully resolved. Overall, the survey of a panel of tumors on a multi-tumor tissue microarray indicated that SPANX-B was expressed in carcinomas of breast, lung, colon and ovary. It was also found that SPANX-B was also preferentially expressed in Cohort C of the Mannheim data set that represented the pattern of genes associated with highly metastatic motif 2.

These data document that healthy humans contain circulating SPANX-B-specific T cell precursors, and that these T cells can be readily expanded to generate both helper CD4+ T cells and cytolytic CD8+ T cells utilizing in vitro immunizations with SPANX-B treated DCs. SPANX-B is not only expressed in human melanomas, but it is also processed and presented on their MHC class I molecules. SPANX-B has at least two immunodominant HLA-A2-restricted Pep-2 and Pep-4 epitopes that alone can be used to elicit SPANX-B-specific CD8+ CTLs. It was demonstrated that SPANX-B-specific CD8+ T cells generated from normal human PBLs can recognize and efficiently kill the HLA-matched human primary melanomas. In addition, one HLA-DR-restricted and immunodominant Pep-9 epitope against was produced and used to readily generate SPANX-B-specific CD4+ T cells from normal human PBLs. The data indicate that SPANX-B is an immunogenic antigen that can readily expand and activate both arms of T cell immunity, helper CD4+ T cells and CD8+ CTLs, to recognize and kill HLA-matched SPANX-B-expressing melanomas.

Example 7

SPANX-B Immunization Induces Robust Humoral Response

Mice were intradermally immunized twice with 25 μg plasmid DNA constructs including MIP-3α-SPANX-B. Sera were tested for SPANX-B antibodies by ELISA assay in 96-well plates coated with the indicated peptides (5 μg/ml).

Figure 7:
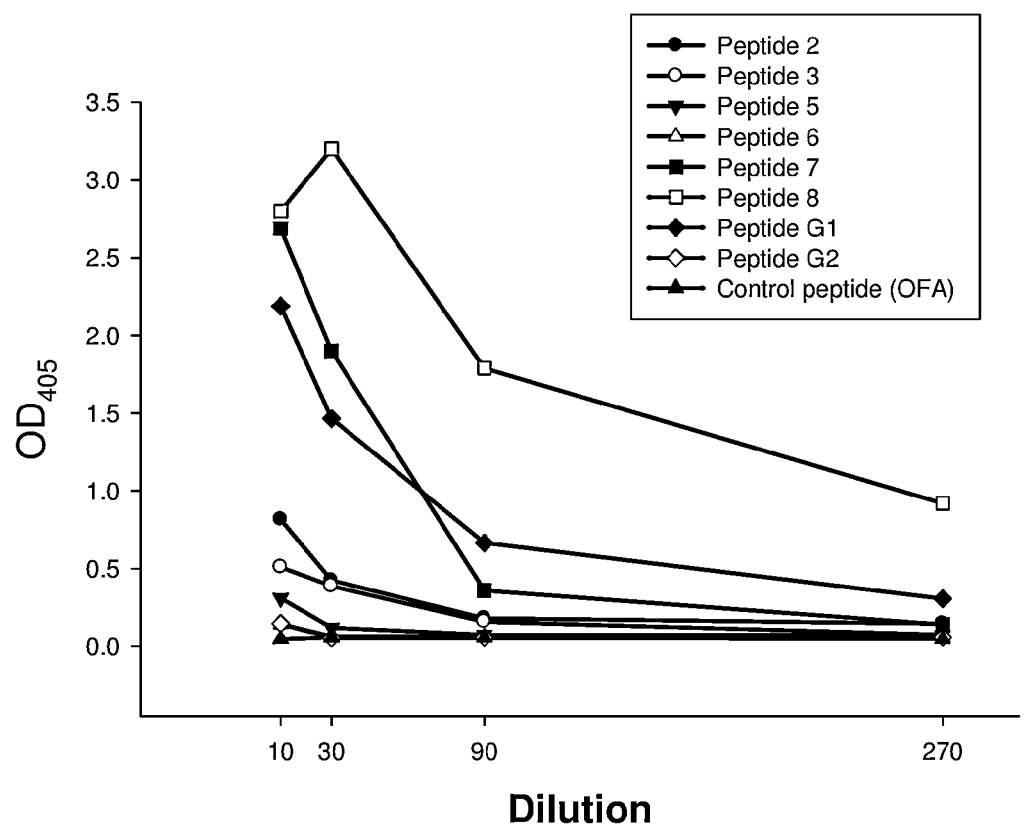
FIG. 7 is a graph showing murine anti-SPANX-B antibody, which was generated from mice DNA immunized with plasmid expressing SPANX-B peptide and a chemoattractant molecule, recognized unique SPANX-B-specific insert of SPANX-B (encoded in Pep-7, Pep-8, Pep-G1, Pep-2, and Pep-3 peptides).

Immunization induced a robust anti-SPANX-B humoral response (FIG. 7). Immunodominant B cell epitopes were localized to two regions of SPANX-B. One was located near the C-terminus, at the overlapping portion of Pep-7 (SEQ ID NO: 7) and Pep-8 (SEQ ID NO: 8). The other was near the N-terminus, encoded by Pep-G1 (SEQ ID NO: 14) and Pep-2 (SEQ ID NO: 2) and Pep-3 (SEQ ID NO: 3).

In view of the many possible embodiments to which the principles of this disclosure may be applied, it should be recognized that the embodiments are only examples and should not be considered a limitation on the scope of the invention. Rather, the scope of the invention is defined by the following claims. We therefore claim as our invention all that comes within the scope and spirit of these claims.

We claim:

1. A method for eliciting a CD8+ T cell immune response in a subject, comprising administering to the subject a therapeutically effective amount of an isolated polypeptide comprising the amino acid sequence set forth as SEQ ID NO: 4, wherein the polypeptide is nine to twelve amino acids in length, thereby producing the CD8+ T cell immune response in the subject.

2. The method of claim 1, wherein the CD8+ T cell immune response comprises inducing cytotoxic T cells that induce lysis of cells expressing SEQ ID NO: 18.

3. The method of claim 1, wherein the subject has a melanoma, a colon carcinoma, an ovarian cancer, a breast cancer, a myeloma, a lung carcinoma, or a renal carcinoma that expresses a polypeptide comprising the sequence set forth as SEQ ID NO: 18.

4. The method of claim 3, wherein the CD8+ T cell immune response decreases the growth of the tumor.

5. The method of claim 1, further comprising administering a therapeutically effective amount of an adjuvant to the subject.

6. A method for inhibiting the growth of a cancer cell, the method comprising, (i) culturing cytotoxic T lymphocytes (CTLs) or CTL precursor cells with an isolated polypeptide comprising the amino acid sequence set forth as SEQ ID NO: 4 wherein the polypeptide is nine to twelve amino acids in length and an antigen presenting cell, to produce activated CTLs or CTLs matured from the CTL precursors that recognize the cancer cell, and (ii) contacting the cancer cell with the activated CTLs or CTLs matured from the CTL precursors, thereby inhibiting the growth of the cancer cell.

7. The method of claim 6, wherein the cancer cell is in vitro.

8. The method of claim 6, wherein the cancer cell is in a subject, and the method comprises administering the cytotoxic T lymphocytes to the subject.

9. The method of claim 8, further comprising administering a therapeutically effective amount of a chemotherapeutic agent to the subject.

10. The method of claim 1, wherein the isolated polypeptide consists of the amino acid sequence of SEQ ID NO: 4.

11. The method of claim 6, wherein the isolated polypeptide consists of the amino acid sequence of SEQ ID NO: 4.

* * * * *

```
                         SEQUENCE LISTING

<160> NUMBER OF SEQ ID NOS: 28

<210> SEQ ID NO 1
  <211> LENGTH: 9
  <212> TYPE: PRT
  <213> ORGANISM: Artificial Sequence
  <220> FEATURE:
  <223> OTHER INFORMATION: Synthetic peptide Pep-1

<400> SEQUENCE: 1

Leu Gln Met Glu Glu Glu Glu Phe Met
  1               5

<210> SEQ ID NO 2
  <211> LENGTH: 9
  <212> TYPE: PRT
  <213> ORGANISM: Artificial Sequence
  <220> FEATURE:
  <223> OTHER INFORMATION: Synthetic peptide Pep-2

<400> SEQUENCE: 2

Glu Ala Asn Glu Ala Asn Lys Thr Met
  1               5

<210> SEQ ID NO 3
  <211> LENGTH: 9
  <212> TYPE: PRT
  <213> ORGANISM: Artificial Sequence
  <220> FEATURE:
  <223> OTHER INFORMATION: Synthetic peptide Pep-3

<400> SEQUENCE: 3

Gly Gln Gln Ser Ser Val Arg Arg Leu
  1               5

<210> SEQ ID NO 4
  <211> LENGTH: 9
  <212> TYPE: PRT
  <213> ORGANISM: Artificial Sequence
  <220> FEATURE:
  <223> OTHER INFORMATION: Synthetic peptide Pep-4

<400> SEQUENCE: 4

Leu Val Val Arg Tyr Arg Arg Asn Val
  1               5

<210> SEQ ID NO 5
  <211> LENGTH: 24
  <212> TYPE: PRT
  <213> ORGANISM: Artificial Sequence
  <220> FEATURE:
  <223> OTHER INFORMATION: Synthetic peptide Pep-5

<400> SEQUENCE: 5

Arg Ser Val Pro Cys Glu Ser Asn Glu Val Asn Glu Thr Met Pro Glu
  1               5                   10                  15

Thr Pro Thr Gly Asp Ser Asp Pro
              20
```

```
<210> SEQ ID NO 6
<211> LENGTH: 24
<212> TYPE: PRT
<213> ORGANISM: Artificial Sequence
<220> FEATURE:
<223> OTHER INFORMATION: Synthetic peptide Pep-6

<400> SEQUENCE: 6

Gln Pro Ala Pro Lys Lys Met Lys Thr Ser Glu Ser Ser Thr Ile Leu
1               5                   10                  15

Val Val Arg Tyr Arg Arg Asn Val
            20

<210> SEQ ID NO 7
<211> LENGTH: 24
<212> TYPE: PRT
<213> ORGANISM: Artificial Sequence
<220> FEATURE:
<223> OTHER INFORMATION: Synthetic peptide Pep-7

<400> SEQUENCE: 7

Lys Arg Thr Ser Pro Glu Glu Leu Val Asn Asp His Ala Arg Glu Asn
1               5                   10                  15

Arg Ile Asn Pro Asp Gln Met Glu
            20

<210> SEQ ID NO 8
<211> LENGTH: 24
<212> TYPE: PRT
<213> ORGANISM: Artificial Sequence
<220> FEATURE:
<223> OTHER INFORMATION: Synthetic peptide Pep-8

<400> SEQUENCE: 8

Glu Asn Arg Ile Asn Pro Asp Gln Met Glu Glu Glu Phe Ile Glu
1               5                   10                  15

Ile Thr Thr Glu Arg Pro Lys Lys
            20

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide Pep-9

<400> SEQUENCE: 9

Arg Ser Val Pro Cys Glu Ser Asn Glu Ala Asn Glu
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide Pep-10

<400> SEQUENCE: 10

Gly Gly Val Lys Arg Ser Val Pro Cys
1               5

<210> SEQ ID NO 11
<211> LENGTH: 9
<212> TYPE: PRT
```

```
<213> ORGANISM: Artificial Sequence
<220> FEATURE:
<223> OTHER INFORMATION: Synthetic peptide Pep-11

<400> SEQUENCE: 11

Glu Phe Met Glu Ile Met Val Glu Ile
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide Pep-12

<400> SEQUENCE: 12

Lys Thr Ser Glu Ser Ser Thr Ile Leu
1               5

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide Pep-9 Mod

<400> SEQUENCE: 13

Arg Ser Ala Pro Cys Ala Ser Ala Glu Val Asn Glu
1               5                   10

<210> SEQ ID NO 14
<211> LENGTH: 21
<212> TYPE: PRT
<213> ORGANISM: Artificial Sequence
<220> FEATURE:
<223> OTHER INFORMATION: Synthetic peptide Pep-G1

<400> SEQUENCE: 14

Lys Arg Ser Val Pro Cys Glu Ser Asn Glu Ala Asn Glu Ala Asn Glu
1               5                   10                  15

Ala Asn Lys Thr Met
            20

<210> SEQ ID NO 15
<211> LENGTH: 21
<212> TYPE: PRT
<213> ORGANISM: Artificial Sequence
<220> FEATURE:
<223> OTHER INFORMATION: Synthetic peptide Pep-G2

<400> SEQUENCE: 15

Ala Asn Glu Ala Asn Glu Ala Asn Lys Thr Met Pro Glu Thr Pro Thr
1               5                   10                  15

Gly Asp Ser Asp Pro
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide MOPC (9)

<400> SEQUENCE: 16

Ala Leu Trp Phe Arg Asn His Phe Val Phe Gly Gly Gly Thr Lys
1               5                   10                  15
```

```
<210> SEQ ID NO 17
<211> LENGTH: 9
<212> TYPE: PRT
<213> ORGANISM: Artificial Sequence
<220> FEATURE:
<223> OTHER INFORMATION: Synthetic peptide influenza HLA-A2 peptide M

<400> SEQUENCE: 17

Gly Ile Leu Gly Phe Val Phe Thr Leu
1               5

<210> SEQ ID NO 18
<211> LENGTH: 103
<212> TYPE: PRT
<213> ORGANISM: Homo sapiens

<400> SEQUENCE: 18

Met Gly Gln Gln Ser Ser Val Arg Arg Leu Lys Arg Ser Val Pro Cys
1               5                   10                  15

Glu Ser Asn Glu Ala Asn Glu Ala Asn Glu Ala Asn Lys Thr Met Pro
            20                  25                  30

Glu Thr Pro Thr Gly Asp Ser Asp Pro Gln Pro Ala Pro Lys Lys Met
        35                  40                  45

Lys Thr Ser Glu Ser Ser Thr Ile Leu Val Val Arg Tyr Arg Arg Asn
    50                  55                  60

Val Lys Arg Thr Ser Pro Glu Glu Leu Leu Asn Asp His Ala Arg Glu
65                  70                  75                  80

Asn Arg Ile Asn Pro Asp Gln Met Glu Glu Glu Glu Phe Ile Glu Ile
                85                  90                  95

Thr Thr Glu Arg Pro Lys Lys
            100

<210> SEQ ID NO 19
<211> LENGTH: 1115
<212> TYPE: DNA
<213> ORGANISM: Homo sapiens

<400> SEQUENCE: 19
agggtgtggc tttgccttgt caccaggagg gtatgcatag ggagggcaag agctctgggc      60
cactgcgaag attcaaaagc tccaaaaacc tactgtagac atcgaagaac caatatatac     120
aatgggccaa caatccagtg tccgcaggct gaagaggagc gtcccctgtg aatccaacga     180
ggccaacgag gccaatgagg ccaacaagac ggtaagattg ttaggttttg aagtgaaggc     240
gagggtgaaa gaaagacaca cagagcgggg gcggctcaaa caacaacaca ggaatattgc     300
gggtgcttgt aggtaggggt gggagggggcc tgggcagtat ggcttgctgc ccggcaggat    360
attgataaga tgttcttatg atcaggtggt ttggccccttt ttctggtgga atatcattgt    420
ggtgttcctt agaacgctgc caagcaagat atgatagga tgtttcttca gttgggcctt     480
tgtccgcctt gcggacaggt ggttaggcag gatgtttctc acggcctgaa ccccatggg     540 atgtttcact ttgaccaagg tctgcaaaat agcaaagaac tgacaaaatg gtgcagtttg    600
gactcacagg tgaccctacc cacgctcctc ttcttcttcc ccatagatcc ctactctgtg    660
cttcaacctt cttcttctct ggatcaaacc ccttcctcaa cctgcattcc ttcttctcat    720 gaagcccct ttgctatcca gtctctatcc tgttcaccca aaataatgtc ctcctggcct     780
ctccctgctt tcttaacaga tgccggagac cccaactggg gactcagacc cgcaacctgc    840
```

```
tcctaaaaaa atgaaaacat ctgagtcctc gaccatacta gtggttcgct acaggaggaa      900
cgtgaaaaga acatctccag aggaactgct gaatgaccac gcccgagaga acagaatcaa      960
ccccgaccaa atggaggagg aggaattcat agaaataacg actgaaagac ctaaaaagta     1020
gcaagaagct acatccctca aacttcggca atgaaaataa agtttgagaa gctgatggct     1080
gtgtatatct ctgcctgttt tctgatgggg ggggt                                1115

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide primer PRSPANXB-Lar-1

<400> SEQUENCE: 20
atgggccaac aatccagtgt                                                   20

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide primer PRSPANXB-
      Lar-R1

<400> SEQUENCE: 21 cttttttaggt ctttcagtcg t                                                21

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide primer SPANX-B
      forward

<400> SEQUENCE: 22
actgtagaca tcgaagaacc                                                   20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide primer SPANX-B
      reverse

<400> SEQUENCE: 23
ttgattctgt tctctcgggc                                                   20

<210> SEQ ID NO 24
<211> LENGTH: 28
<212> TYPE: DNA
<213> ORGANISM: Artificial Sequence
<220> FEATURE:
<223> OTHER INFORMATION: Synthetic oligonucleotide primer PRuGAPDH-1

<400> SEQUENCE: 24
tgtggaaggg ctcatgacca cagtccat                                          28

<210> SEQ ID NO 25
<211> LENGTH: 24
<212> TYPE: DNA
<213> ORGANISM: Artificial Sequence
<220> FEATURE:
```

```
<223> OTHER INFORMATION: Synthetic oligonucleotide primer PRuGAPDH-R1

<400> SEQUENCE: 25
gcctgcttca ccaccttctt gatg                                          24

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide modified Pep-2a

<400> SEQUENCE: 26

Asn Leu Ala Asn Glu Ala Asn Lys Val
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide modified Pep-1a

<400> SEQUENCE: 27

Leu Leu Met Glu Glu Glu Glu Phe Ile
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide modified Pep-1b

<400> SEQUENCE: 28

Leu Gln Met Glu Glu Glu Glu Phe Ile
1               5
```